(12) United States Patent
Couch et al.

(10) Patent No.: US 8,958,617 B2
(45) Date of Patent: *Feb. 17, 2015

(54) DOSE ESTIMATION SERVICE SYSTEM CONFIGURED TO SUPPORT MULTIPLE COMPUTERIZED MEDICAL IMAGING SCAN PROVIDERS

(75) Inventors: Gregory Couch, Ontario (CA); James Couch, Toronto (CA)

(73) Assignee: Bayer HealthCare LLC, Indianola, PA (US)

( * ) Notice: Subject to any disclaimer, the term of this patent is extended or adjusted under 35 U.S.C. 154(b) by 305 days.

This patent is subject to a terminal disclaimer.

(21) Appl. No.: 13/315,208

(22) Filed: Dec. 8, 2011

(65) Prior Publication Data

US 2012/0150505 A1    Jun. 14, 2012

Related U.S. Application Data

(60) Provisional application No. 61/420,834, filed on Dec. 8, 2010.

(51) Int. Cl.
*G06K 9/00* (2006.01)
*A61B 6/03* (2006.01)
*A61B 6/00* (2006.01)
*G06F 19/00* (2011.01)

(52) U.S. Cl.
CPC ............... *A61B 6/032* (2013.01); *A61B 6/488* (2013.01); *A61B 6/5229* (2013.01); *A61B 6/542* (2013.01); *G06F 19/3437* (2013.01); *A61B 6/563* (2013.01); *A61B 6/583* (2013.01)
USPC ........................................ 382/131

(58) Field of Classification Search
None
See application file for complete search history.

(56) References Cited

U.S. PATENT DOCUMENTS

| 5,341,292 | A | 8/1994 | Zamenhof | |
|---|---|---|---|---|
| 5,844,241 | A | 12/1998 | Liu et al. | |
| 6,345,112 | B1 | 2/2002 | Summers et al. | |
| 6,771,374 | B1 * | 8/2004 | Rangarajan et al. | 356/445 |
| 7,082,183 | B2 * | 7/2006 | Toth et al. | 378/16 |
| 7,792,249 | B2 | 9/2010 | Gertner et al. | |
| 2001/0027262 | A1 | 10/2001 | Mistretta et al. | |
| 2003/0233039 | A1 * | 12/2003 | Shao et al. | 600/407 |
| 2008/0103834 | A1 * | 5/2008 | Reiner | 705/3 |

(Continued)

FOREIGN PATENT DOCUMENTS

WO    2011137374    11/2011

OTHER PUBLICATIONS

Bacher, Klaus et al. "Patient-Specific Dose and Radiation Risk Estimation in Pediatric Cardiac Catheterization," Circulation Journal of the American Heart Association, Dec. 20, 2004, 8 pages.*

(Continued)

*Primary Examiner* — Chan Park
*Assistant Examiner* — Ryan P Potts
(74) *Attorney, Agent, or Firm* — Jim Stevenson; Patterson & Sheridan, LLP

(57) ABSTRACT

Patient radiation exposure during computerized tomography (CT) scans is estimated. More specifically, efficient approaches for generating a suitable patient model which may be used for estimating the radiation dose absorbed by a patient receiving a CT scan, for estimating a patient dose by interpolating the results of multiple simulations, and for a service provider to host a dose estimation service made available to multiple CT scan providers.

18 Claims, 11 Drawing Sheets

(56) References Cited

U.S. PATENT DOCUMENTS

2008/0292055 A1 11/2008 Boone
2008/0298540 A1 12/2008 Serban et al.
2010/0288916 A1 11/2010 Cho et al.

OTHER PUBLICATIONS

Rohr, K. et al. "Point-Based Elastic Registration of Medical Image Data Using Approximating Thin-Plate Splines," Visualization in Biomedical IMaging Lecture Notes in Computer Science, vol. 1131, 1996, 11 pages.*

Jarry, G. et al. "A Monte Carlo-based Method to Estimate Radiation Dose from Spiral CT: from Phantom Testing to Patient-Specific Models," Phys. Med. Biol. 48, Jul. 30, 2003, 20 pages.*

International Search Report and Written Opinion for International Application No. PCT/CA2011/001381 dated Apr. 12, 2012.

Michael Sandborg, et al.; Schemes for the optimization of chest radiography using a computer model of the patient and x-ray imaging system; Medical Physics, vol. 28, No. 10, pp. 2007-2019; Oct. 2001.

* cited by examiner

DOSE ESTIMATION SERVICE SYSTEM CONFIGURED TO SUPPORT MULTIPLE COMPUTERIZED MEDICAL IMAGING SCAN PROVIDERS

CROSS REFERENCE TO RELATED APPLICATIONS

This application claims benefit of U.S. Provisional Patent Application Ser. No. 61/420,834 filed Dec. 8, 2010, which is incorporated herein by reference in its entirety.

FIELD OF THE INVENTION

Embodiments of the invention are generally directed to approaches for estimating patient radiation exposure during computerized tomography (CT) scans.

BACKGROUND

As is known, a CT scanning system uses ionizing radiation (X-rays) to generate images of tissues, organs, and other structures within a body. The X-ray data resulting from a CT scan may be converted into images on a computer display screen. For example, the CT scan provides a collection of data used to create a three dimensional (3D) volume corresponding to the scanned portion of a patient's body. The 3D volume is then sliced to create images of body tissue at small intervals along an axis of the patient's body. Such slices may include both lateral and transverse slices (as well as other slices) depending on the tissues or structures being imaged.

The use of CT scans and ionizing radiation for medical imaging has grown exponentially over the past decade. And modern techniques such as CT scanning provide much more detailed and valuable diagnostic information than conventional X-ray imaging. Concurrently however, patients are being exposed to substantially larger doses of radiation. For example, a typical chest CT will expose a patient to anywhere between 100-250 times the dose of a conventional chest X-Ray depending on the voltage and current of the CT scanning system, the protocol followed to perform the procedure, and the size and shape of the patient being scanned.

Despite the increased use of CT scans (and resulting exposure to radiation) the amount of radiation a patient is exposed to during a procedure, and importantly, the cumulative dose over many procedures are not parameters are regularly tracked for a patient, and nor are these parameters readily accessible part of the patient's medical records. This occurs in part because the amount of radiation absorbed by internal organs and tissues cannot be measured in live patients directly as part of a CT exam, and results obtained from cadavers, while more accurate, do not correspond well to dose absorption in live tissues.

Similarly, approaches for estimating dose used currently also provide inaccurate results. For example, one approach is to rely on a limited number of physical imaging phantoms to represent a given patient. However, the available imaging phantoms do not adequately represent the broad variation in people's size and weight in the population of individuals receiving CT scans. As a result, single point surface measurements are what is currently done in the majority of cases where dose is estimated at all. However, this leads to both poor and widely varying results, depending on where the single point dose is measured. More generally, surface measurements of radiation exposure do not provide an accurate measure of actual absorption for internal tissues, organs, and structures.

SUMMARY

Embodiments provide techniques for estimating patient radiation exposure during computerized tomography (CT) scans. One embodiment provides a computer-implemented method for providing a plurality medical imaging providers with estimates of radiation dose absorbed by individuals receiving imaging scans. This method may generally include receiving, from one of the medical imaging providers, a request for an estimate of radiation dose absorbed by an individual in receiving an imaging scan. The request identifies an imaging phantom, a transformation for deforming the imaging phantom, and a set of parameters describing the imaging scan and an image scanning apparatus being used to perform the imaging scan. This method may also include deforming the imaging phantom based on the transformation and evaluating a plurality of dose estimation simulations estimating radiation dose absorption. Upon determining, based on the evaluation, that two or more of the simulations match the received set of parameters and deformed imaging phantom within a specified tolerance measure, the estimates of radiation dose are interpolated in the two or more simulations to determine the estimate of radiation dose absorbed by the individual in receiving the imaging scan. This method may also include returning, to the medical imaging provider, the interpolated estimate of patient dose.

In a particular embodiment, the imaging scan is a computerized tomography (CT) scan and the interpolation is a multivariate scatter interpolation, e.g., Shepard's method. Upon determining that the plurality of simulations do not include at least two simulations matching the received set of parameters and received imaging phantom within the specified tolerance measure, then the method may also include performing a simulation of the imaging scan using the deformed imaging phantom and the set of parameters, estimating, based on the simulation, amounts of radiation absorbed by the individual as a result of performing the imaging scan, and adding the performed simulation to the plurality of dose estimation simulations.

Additional embodiments include a computer-readable storage medium storing an application, which, when executed on a processor, performs the above recited method as well as a system having a processor and a memory storing an enterprise information asset management application program, which, when executed on the processor, performs the above recited method.

BRIEF DESCRIPTION OF THE DRAWINGS

So that the manner in which the above recited aspects are attained and can be understood in detail, a more particular description of embodiments of the invention, briefly summarized above, may be had by reference to the appended drawings. Note however, the appended drawings illustrate only typical embodiments invention and are therefore not limiting of its scope, for the invention may admit to other equally effective embodiments.

DETAILED DESCRIPTION

Figure 1:
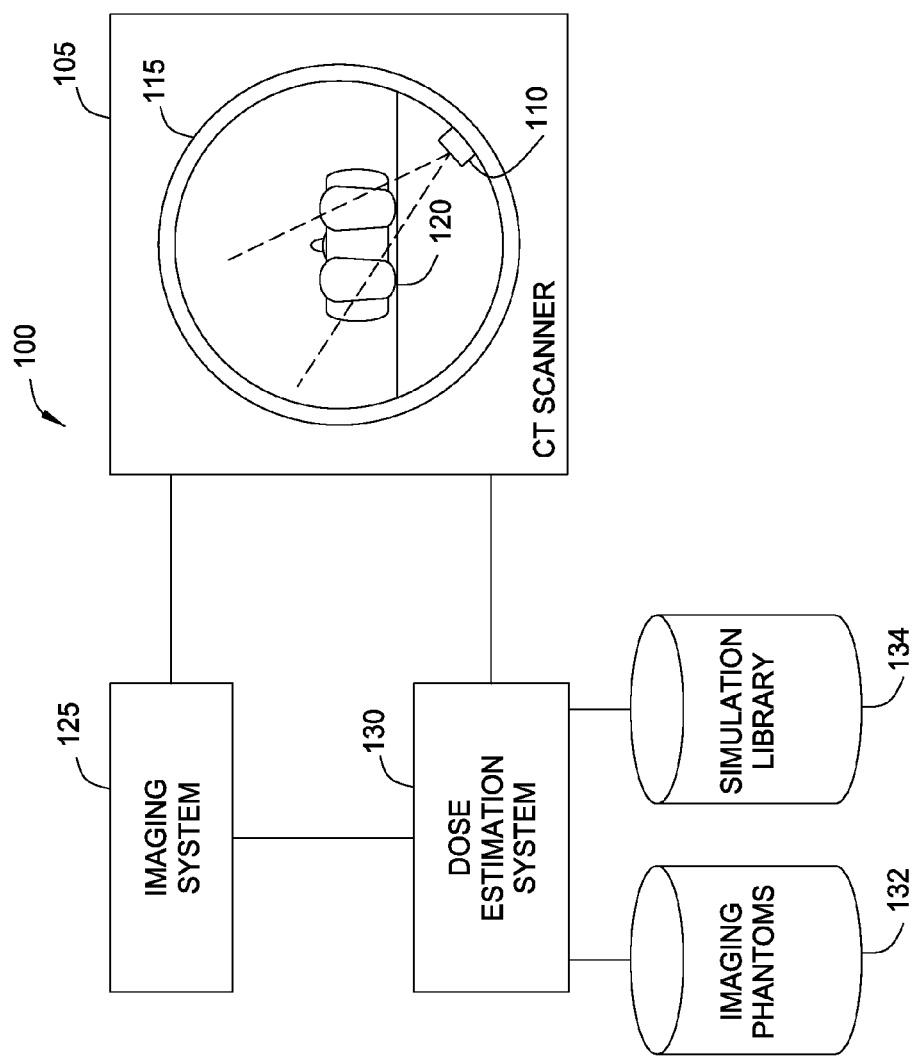
FIG. 1 illustrates an example of a CT scanning system and related computing systems configured to provide estimates of patient radiation dose, according to one embodiment of the invention.

Embodiments of the invention are generally directed to approaches for estimating patient radiation exposure during computerized tomography (CT) scans. More specifically, embodiments of the invention provide efficient approaches for generating a suitable patient model used to make such an estimate, to approaches for estimating patient dose by interpolating the results of multiple simulations, and to approaches for a service provider to host a dose estimation service made available to multiple CT scan providers. As described in detail below, the dose management system provides a single system for tracking radiation dose across modalities and to present information to practitioners in a meaningful and easily understood format. Routine consideration of cumulative dose in ordering diagnostic imaging tests may lead to a more informed decision-making process and ultimately benefit patient safety and care.

In one embodiment, a virtual imaging phantom is generated to model a given patient receiving a CT scan. The virtual imaging phantom may be generated by deforming an existing mathematical phantom to better match the size, shape, and/or organ positions of a patient being exposed to radiation in a CT scan. Initially, a mathematical phantom may be selected based on, e.g., an age and gender of the patient. Patient specific geometry may be achieved by deforming the selected mathematical phantom using transformations obtained by analyzing scout image localizers of that patient. Note, in this context, as understood by one of ordinary skill in the art, a "localizer" generally refers to a 2D image projection of a patient (typically an anterior/posterior X-ray image and/or a lateral X-ray image). In such an approach, the selected mathematical phantom may have its own reference set of localizer images. The reference images for a given virtual phantom are selected to match the geometry, size and positioning of that phantom (e.g., arms up or at the side) and may be selected from imaging obtained from multiple individuals.

Image registration techniques are then used to map points in the localizer image of the patient to points in the reference image (or images) associated with the virtual phantom. Doing so results in a set of transformations that can be used to deform the virtual phantom to better match the geometry of the patient. A similar approach involves using a reference set of 3D data (selected CT scans) for the phantom and using 3D image registration techniques to map points in a CT scan of a given patient to points in reference CT scans associated with a given phantom.

Similarly, image segmentation may be used to identify a 3D volume within a CT scan corresponding to organs, tissues, or structures of interest in a CT scan of a patient. The 3D volume may be a bounding box, or a more precise 3D volume believed to represent an organ, etc. Once identified, a displacement may be determined between the position of the organ in the phantom and the corresponding position in the patient's CT scan. Instead of working on individual image points (as in the 2D/3D image registration techniques) the image segmentation approach works by using larger 3D volumes from the CT image as data points to determine a transformation from a virtual phantom and a given patient.

In each of these cases, the resulting hybrid phantom provides a much more accurate mathematical representation of a particular patient to use in a dose simulation than the unmodified phantoms alone. Once the transformations are determined, the hybrid virtual phantom may be used to simulate a given CT procedure for the patient. For example, well known Monte Carlo simulation techniques have been developed for estimating organ absorbed dose for a virtual phantom. Such simulation techniques use the virtual phantom (as transformed relative to a given patient), along with a number of settings related to the CT scanner model and procedure to be performed in order to compute accurate estimates of organ absorbed dose. For example, a CT scanner may be modeled using kVp, i.e., peak kilovoltage, X-ray generator target angle, fan angle, collimation, slice thickness, focus to axis distance, flat filters (material and thickness), and beam shaping filters (material and geometry). Of course, these (and other parameters) may be selected as available or as needed to suit the needs of a particular case.

However, estimating organ absorbed organ dose using a Monte Carlo simulation can require significant amounts of computing time, much longer than required to perform an actual CT scan. Given the high utilization of CT scanning systems at many imaging facilities, in cases where an estimate of total cumulative dose should not exceed a prescribed maximum, this delay is simply not tractable. Even in cases where the estimate is not used prior to performing a given procedure, unless the estimates of patient dose can be determined in relatively the same order of time as required to perform a procedure, then maintaining a record of dose estimation for a given scanning system becomes intractable—as the simulations will simply fall further and further behind the current scans being performed. This problem grows exponentially for a SaaS provider hosting a dose estimation service in the cloud for multiple imaging facilities.

Accordingly, in one embodiment, estimates of patient dose determined for a given procedure may be generated by interpolating between two (or more) previously completed simulations. If no "close" simulations are available, then the hybrid virtual phantom, CT scanner and procedure data may be added to a queue of full Monte Carlo simulations to be performed. Over time, a large library of simulations allows for dose estimates to be provided in real time as procedures are scheduled and preformed. Doing so allows cumulative dose amounts for a given patient to be captured, as well as cumulative dose limits to be observed.

Further, in one embodiment, a Software as a service (SaaS) or cloud provider model may be used to perform the dose estimates, maintain a library of computed simulations, as well as run the Monte Carlo simulations. In such a case, a CT scan provider may supply the SaaS provider with the parameters of a given CT procedure. For example, client software (or even a secure web-based portal) at an imaging center may be used to supply the SaaS provider with a selected virtual phantom, along with transforms used to create a hybrid phantom modeling a particular individual and the equipment and protocol to be used in performing a CT procedure. Once received, the service provider can select the appropriate simulations from the library to interpolate and return an estimate of patient organ absorbed dose to the imaging center.

Importantly, the SaaS provider need not receive any actual identifying information about a given individual or patient receiving a CT scan. Instead, the SaaS provider receives only information related to a virtual phantom and a CT system/procedure. As a result, the operations of the service provider may not require compliance with a variety of laws and/or regulations related to the privacy of personal health information. Further, by providing dose estimates for multiple imaging centers, the resulting simulation library becomes more diverse and much more likely to find candidates for interpolation than a simulation library generated solely from scanning procedures performed by a single imaging center. Further still, centralizing the simulation library and Monte Carlo simulations allows improvements to the phantoms, a Monte Carlo simulation engine, and interpolation techniques to be shared by all imagining centers using the cloud based service. Lastly, this approach leaves it to the imaging center to maintain information tying cumulative dose to specific patients. Allowing actual patient data to remain with each individual provider. At the same time, the SaaS provider may, of course, communicate with the imaging centers using a variety of standardized protocols for image and data exchange, including, e.g., digital Imaging and Communications in Medicine (DICOM), Picture Archiving and Communication Systems (PACS), Health Level Seven International (HL7) standards, ICD-9, ICD-10 diagnosis and procedure codes, etc.

Additionally, the following description references embodiments of the invention. However, it should be understood that the invention is not limited to specific described embodiments. Instead, any combination of the following features and elements, whether related to different embodiments or not, is contemplated to implement and practice the invention. Furthermore, although embodiments of the invention may achieve advantages over other possible solutions and/or over the prior art, whether or not a particular advantage is achieved by a given embodiment is not limiting of the invention. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus or device.

The flowchart and block diagrams in the Figures illustrate the architecture, functionality and operation of possible implementations of systems, methods and computer program products according to various embodiments of the present invention. In this regard, each block in the flowchart or block diagrams may represent a module, segment or portion of code, which comprises one or more executable instructions for implementing the specified logical function(s). In some alternative implementations the functions noted in the block may occur out of the order noted in the figures. For example, two blocks shown in succession may, in fact, be executed substantially concurrently, or the blocks may sometimes be executed in the reverse order, depending upon the functionality involved. Each block of the block diagrams and/or flowchart illustrations, and combinations of blocks in the block diagrams and/or flowchart illustrations can be implemented by special-purpose hardware-based systems that perform the specified functions or acts, or combinations of special purpose hardware and computer instructions.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g., an amount of storage space consumed by a user or a number of virtualized systems instantiated by the user). A user can access any of the resources that reside in the cloud at any time, and from anywhere across the Internet. In context of the present invention, a service provider may provide imaging centers with estimates of patient dose in both predictive and reporting perspectives. For example, a dose estimation interface may be used to submit virtual phantom and CT data to the cloud based provider.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Further, particular embodiments of the invention described below rely on a particular example of a computed tomography CT scanning system using a client-server architecture to provide dose estimation to a set of imaging, It should be understood, however, that the techniques described herein may be adapted for use with other medical imaging technology relying on exposing individuals to limited radiation doses as part of the imaging procedure (e.g., PET scans, conventional X-ray imaging, and fluoroscopy and angiography, etc.).

FIG. 1 illustrates an example of a CT scanning environment 100 and related computing systems configured to provide estimates of patient radiation dose, according to one embodiment of the invention. As shown, the CT scanning environment 100 includes a CT scanning system 105, an imaging system 125, and a dose estimation system 130. Additionally, the dose estimation system 130 includes a database of imaging phantoms 132 and a simulation library 134.

As is known, the CT scanner 105 provides a device used to bombard a subject 120 with X-rays from an X-ray source 110. The X-rays emitted from X-ray source 110 pass through tissues, organs, and structures of the subject 120 at different rates (some of which is absorbed by such tissues organs and structures) depending on the density and type of matter which the X-rays pass through. Sensors disposed with a ring 115 detect the amount of radiation that passes through the subject 120. The resulting sensor information is passed to imaging system 125. The imaging system 125 provides a computing device configured to receive, store, and generate images from the sensor data obtained from the CT scanner.

The imaging system 125 allows an operator to perform a given CT procedure as well as receive data obtained carrying out CT scans. For example, the imaging system 125 may be configured to "window," various body structures, based on their ability to block X-rays emitted from source 110. CT scanning images (often referred to as "slices") are typically made relative to an axial or transverse plane, perpendicular to the long axis of the body. However, CT scanner 105 may allow the imaging data to be reformatted in various planes or as volumetric (3D) representations of structures. Once a CT scan is performed, the imaging data generated by CT scanner 105 may be stored allowing the resulting scan images to be reviewed or evaluated in other ways. In one embodiment, imaging data may be formatted using the well known DICOM standard and stored in a PACS repository.

In one embodiment, the dose estimation system 130 provides a computing system and software applications configured to estimate an amount of patient absorbed dose for a given patient receiving a given CT scan. Note, such an estimate may be made in a predictive sense (i.e., before performing a scan) but may be made after the fact as well.

In the predictive case, the dose estimation system 130 may provide an estimate of patient dose prior to performing a CT scan. Further, in one embodiment, dose estimation system 130 may be configured to automatically generate alerts based on configurable thresholds. The criteria for the generating an alert may use a rule engine that can take into account age, gender, ICD9/ICD10 encoding, and other information about a given patient or procedure (e.g., a specified cumulative dose limit). More generally, dose thresholds may be flexible enough to reflect any legislative, institutional, or treatment requirements for dose monitoring. In one embodiment, the resulting dose estimates may be stored as part of a patient's medical records/history maintained by an imaging center, hospital, or other provider.

Further, dose thresholds may optionally be used to create an incident reports routed to the appropriate practitioners. Incident reports may include a description of a procedure and any dose estimates that exceed a rule or threshold along with any supplementary information needed to provide context for practitioner intervention or decision making. In one embodiment, such a report may be printed/emailed using a customizable XML template.

Imaging phantoms 132 may provide accepted mathematical models of portions of human tissue, organs, structures, etc. For example, imaging phantoms 132 may provide a set of non-uniform rational basis spline (NURBS) used to create a three dimensional (3D) model of a human body (or portion thereof). Alternatively, the imaging phantoms may be represented using constructive solid geometry (CSG) or other mathematical representation. Different imaging phantoms 132 may be provided to generally model individuals based on age and gender. However, as noted above, the virtual geometry and body shape of an imaging phantom selected based on just age and/or gender may (or may not) correspond to the size, shape and organ positions of an actual person having a CT procedure. Accordingly, in one embodiment, the dose estimation system 130 may be configured to deform a virtual phantom to better model a particular patient. Example embodiments for deforming a virtual imaging phantom 122 are discussed in greater detail below.

Once an imaging phantom is deformed to model a particular individual, dose estimation system 130 may perform a simulation to estimate an amount of first pass dose deposition resulting from a given CT scanning procedure. For example, in one embodiment, a Monte Carlo simulation may be performed using the CT scanning parameters, CT procedure parameters, and the deformed phantom to arrive at an estimation of dose. However, other simulation approaches could be used as well. The results of a given dose estimation simulation may be stored in the simulation library 134.

For example, the CT scanner may be parameterized for a simulation based on X-ray tube current and voltage, CT Scanner mode, kVp, X-ray generator target angle, fan angle, collimation, slice thickness, focus to axis distance, flat filters (material and thickness), beam shaping filters (material and geometry). While a variety of approaches may be used in the simulation process, in one embodiment, kVp, target angle and filtration are used to model the X-ray spectrum as described in "Computation of bremsstrahlung X-ray spectra over an energy range 15 KeV to 300 KeV," W. J. Iles, Regne Unit. National Radiological Protection Board, NRPB, 1987.

In addition, focus to axis distance determines the distance of the X-ray source to the axis of rotation and fan angle determines how widely the beam spreads on the slice plane. Of course, these (and other parameters) may be selected as available or as needed to suit the needs of a particular case. Typically however, energy deposition is stored per slice for each anatomical region defined in the phantom. A normalization simulation of a CTDIvol phantom may be performed for each CT model. This per-slice energy deposition information, combined with the masses for each anatomical region is sufficient for calculating absorbed dose to each region for a given scan region (using a sub-set of our full body simulation).

However, performing a Monte Carlo simulation typically requires substantial processing time to complete—much longer than performing the CT scan itself. Accordingly, in one embodiment, the dose estimation system 130 estimates dose by interpolating between two (or more) simulations in the simulation library 134. For example, a first pass patient dose may be calculated using multivariate scatter interpolation of existing simulation data. Patient dose information is refined as more applicable simulations are added. Similarly, new scanner models may be added to the simulation library 134 as calibration measurements and specifications of these scanners are obtained.

The simulation library 134 provides a database of Monte Carlo simulation results. In one embodiment, the simulation library 134 stores information on the dose/energy deposition to a set of phantoms, both as supplied and as deformed for individual patients, for a collection of supported medical imaging scanners, e.g., CT, RF, XA imaging modalities, among others. In one embodiment, the simulation library 134 is used to provide real time look-up and/or calculations of dose distributions given acquisition parameters, patient description, and scan region.

As noted, the simulation library 134 may be augmented automatically over time as additional Monte Carlo simulations are completed. For example, simulations to perform may be added to a queue as CT scan examinations occur. Priority may be given to simulations in an area with sparse existing data points. Doing so improves the probability of identifying simulations to interpolate, i.e., improves the simulation "space" covered by the simulation library 134. Similarly, more simulations available in simulation library 134 allow more stringent thresholds for selecting simulations to interpolate in a given case—leading to greater accuracy in dose estimates.

Note, while shown in FIG. 1 as part of a CT scanning environment 100, the dose estimation system 130 (and phantoms 132 and library 134) may be provided as a hosted service accessed by/from the a CT scanning environment 100. For example, an imaging center may use a client interface on the imaging system 125 (e.g., a secure web portal or dedicated client application) to interact with a hosted dose estimation provider. An example of such an embodiment is discussed in greater detail below with respect to FIGS. 11 and 12.

Figure 2:
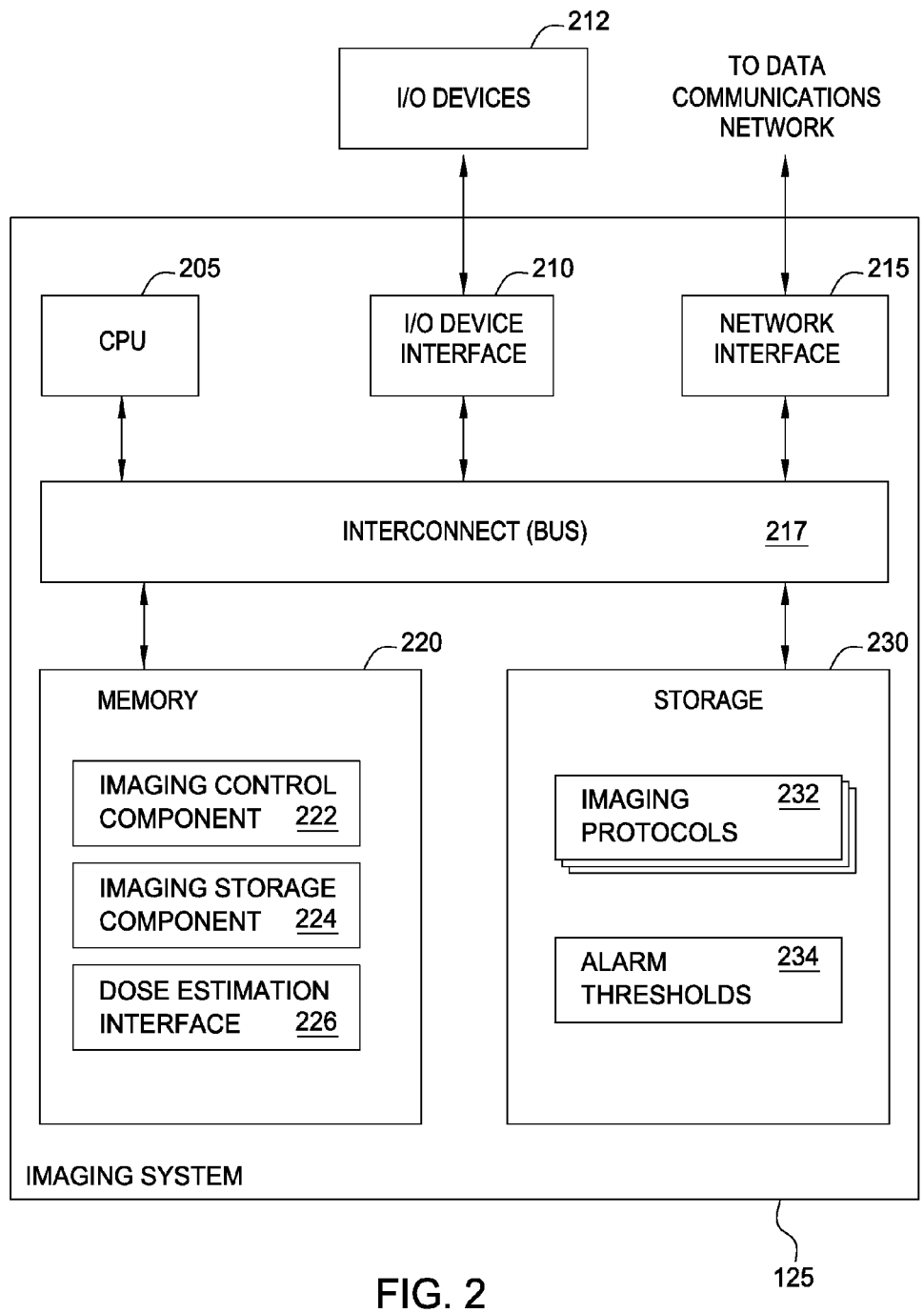
FIG. 2 illustrates an example an imaging system used to obtain CT scan data, according to one embodiment.

FIG. 2 illustrates an example an imaging system 125 used to obtain CT scan data and mange estimates of patient dose, according to one embodiment. As shown, the imaging system 125 includes, without limitation, a central processing unit (CPU) 205, a CT system interface 214 network interface 215, an interconnect 217, a memory 225 and storage 230. The Imaging system 125 may also include an I/O device interface 210 connecting I/O devices 212 (e.g., keyboard, display and mouse devices) to the imaging system 125.

CPU 205 retrieves and executes programming instructions stored in the memory 225. Similarly, the CPU 205 stores and retrieves application data residing in the memory 225. The interconnect 217 facilitates transmission of programming instructions and application data between the CPU 205, I/O devices interface 210, storage 230, network interface 215, and memory 225. CPU 205 is included to be representative of a single CPU, multiple CPUs, a single CPU having multiple processing cores, and the like. And the memory 225 is generally included to be representative of a random access memory. The storage 230 may be a disk drive storage device. Although shown as a single unit, the storage 230 may be a combination of fixed and/or removable storage devices, such as disc drives, solid state storage devices (SSD), network attached (NAS), or a storage area-network (SAN). Further, storage 230 (or connections to storage repositories) may conform to a variety of standards for data storage related to health care environments (e.g., a PACS repository).

As shown, the memory 220 includes an imaging control component 222, an image storage component 224, and a dose estimation interface 226. And the storage 235 imaging protocols 232 and alarm thresholds 234. The imaging control component 222 corresponds to software applications used to perform a given CT scanning procedure—as specified by an imaging protocol 232. The imaging protocols 232 generally specify position, time, and duration for performing a specific CT procedure using a particular scan modality. The image storage component 224 provides software configured to store images and CT data derived while performing a given CT procedure or that interacts with a suitable storage repository to store such images and data. For example, CT scan data may be sent over a TCP/IP connection (via network interface) to/from a PACS repository.

The dose estimation interface 226 provides software components configured to interface with the dose estimation system 130 to obtain an estimate of patient dose that may result from a particular CT procedure. As noted, in one embodiment, the dose estimation interface 226 may interact with systems local to the CT imaging environment. However, in an alternative embodiment, the dose estimation interface 226 may interact with a hosted service provider. In such a case, the interface 226 may send requests for estimates of patient dose to the hosted service provider. Further, such request may indicate an imaging phantom, transforms to that phantom, and the CT scanning equipment and protocols being followed for a given imaging scan. In either case, when being used in a predictive sense (i.e., before performing a procedure), the estimate of patient dose may be compared against alarm thresholds and rules to determine whether any alarms should issue prior to a given procedure being performed (e.g., an alarm indicating that a given procedure will (or would be likely to) exceed a cumulative dose limit for a given patient, organ or body part, etc.

Figure 3:
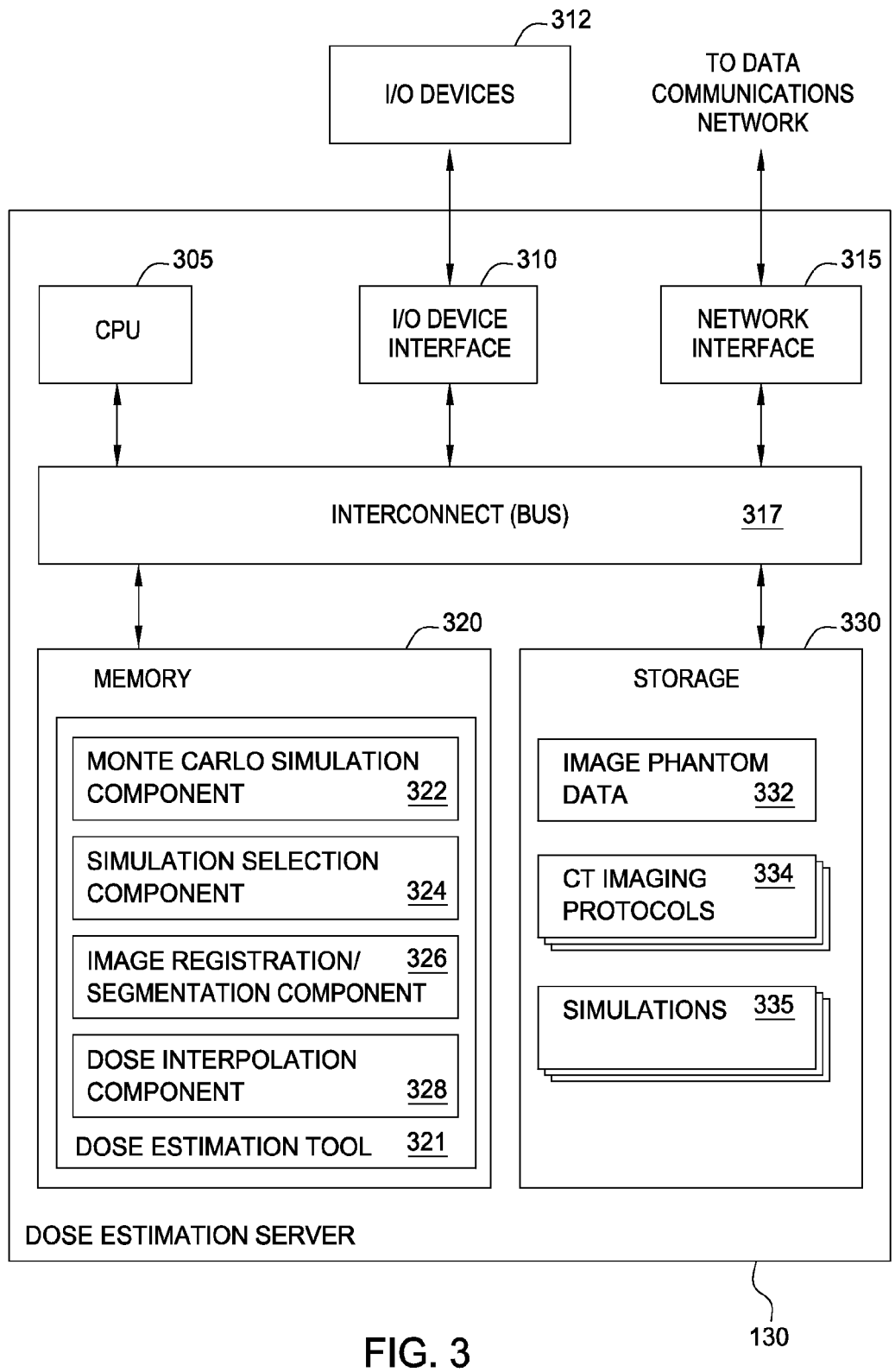
FIG. 3 illustrates an example of a dose estimation system used to estimate and track cumulative patient dose, according to one embodiment.

FIG. 3 illustrates an example of a dose estimation system 130 used to estimate and track cumulative patient dose, according to one embodiment. As shown, the dose estimation system 130 includes, without limitation, a central processing unit (CPU) 305, a network interface 315, an interconnect 320, a memory 325 and storage 330. The dose estimation system 130 may also include an I/O devices interface 310 connecting I/O devices 312 (e.g., keyboard, display and mouse devices) to the dose estimation system 130.

Like CPU 205, CPU 305 is included to be representative of a single CPU, multiple CPUs, a single CPU having multiple processing cores, etc., and the memory 325 is generally included to be representative of a random access memory. The interconnect 317 is used to transmit programming instructions and application data between the CPU 305, I/O devices interface 310, storage 330, network interface 315 and memory 325. The network interface 315 is configured to transmit data via the communications network, e.g., to receive requests from an imaging system for dose estimation. Storage 330, such as a hard disk drive or solid state (SSD) storage drive, may store non-volatile data.

As shown, the memory 320 includes a dose estimation tool 321, which provides a set of software components. Illustratively, the dose estimation tool 321 includes a Monte Carlo simulation component 322, a simulation selection component 324, an image registration/segmentation component 326, and a dose interpolation component 328. And storage 330 contains imaging phantom data 332, CT imaging protocols 334 and simulation library 336.

The Monte Carlo simulation component 322 is configured to estimate patient radiation dose based on a simulation using imaging phantom data 322 and a particular set of CT imaging equipment and a specified imaging protocol 334. As noted, in one embodiment, the imaging phantom data 332 may be deformed or otherwise transformed to better match the physical characteristics of a given patient.

The image registration/segmentation component 326 may be configured to determine a set of transforms for deforming the imaging phantom data 332 prior to performing a Monte Carlo simulation using that phantom. For example, the image registration/segmentation component 326 may evaluate a reference or localizer image associated with a phantom along with a scout localizer image of a patient using image registration techniques. Image registration is the process for aligning two images into a common coordinate system. An image registration algorithm determines a set of transformations to set a correspondence between the two images. Once the transforms between the scout image of the patient and a reference image of a phantom is determined, the same transformations may be used to deform the phantom. Such deformations may scale, translate and rotate the geometry of the virtual phantom to correspond to the patient.

In another embodiment, image segmentation is used to identify a size and a relative position of organs, tissues, and anatomical structures of a patient. In such a case, available CT scan data for a patient may be segmented to identify geometric volumes believed to correspond to an organ (or other structure of interest). For example, in one embodiment, image segmentation may be used to identify a bounding box believed to contain a particular organ or structure. Other segmentation approaches may be used to provide a more definitive 3D volumetric region corresponding to an organ or structure. Once identified, this information is used to displace the geometry of the corresponding organ (or structure of interest) in the virtual phantom.

Note, although shown as part of the dose estimation server 130, in one embodiment, the image registration/segmentation component 326 is part of the imaging system 125, or otherwise part of the computing infrastructure at an imaging facility. Doing so allows a provider hosting a dose estimation service to receive transforms for deforming a given virtual phantom, without also receiving any information that could be used to identify a patient receiving a CT scan at an imaging facility. This approach may simplify (or eliminate) certain legal or regulatory requirements associated with entities processing protected health information or medical records.

After completing a Monte Carlo simulation, the resulting estimates of patient dose, along with the parameters supplied to the simulation component 322, are stored in the simulation library 335. In turn, the dose interpolation component 328 is used to determine an estimate of patient dose from the simulations in the simulation library 335, without performing a complete Monte Carlo simulation. To do so, the simulation selection component 324 may compare the parameters of a CT scan, the equipment used to perform the CT scan, and the imaging phantom deformed to represent a particular individual. This information is used to identify a set of two or (or more) simulations to interpolate. While a variety of approaches may be used, in one embodiment, the selection component 324 may use a distance measure to compare the deformed phantom, the CT procedure, and CT equipment with ones in the simulation library 335. In one embodiment, the top 2 (or top N) choices are selected for interpolation. Alternatively, any simulations with an overall similarity measure within a specified threshold are selected for interpolation. In such a case, by tuning the thresholds more, or less, simulations are used for interpolation.

Given the set of parameters describing the scanner and patient for an examination, (kVp, target angle, gantry tilt, height, weight, etc.) the system allows customizable tolerances to be set for each variable (e.g., actual kVp is within 10 kV of simulation). When searching for simulations, only those simulations within tolerance for all given parameters will be factored into the calculation. In one embodiment, the simulation results may be interpolated using the known Shepard's method. The standard deviation across the set of simulation results is used as a measure of uncertainty (e.g. for the set of 5 simulations used, absorbed dose to the breasts has a SD of 0.2 mSv and absorbed dose to the liver has a SD of 0.15 mSv).

Figure 4:
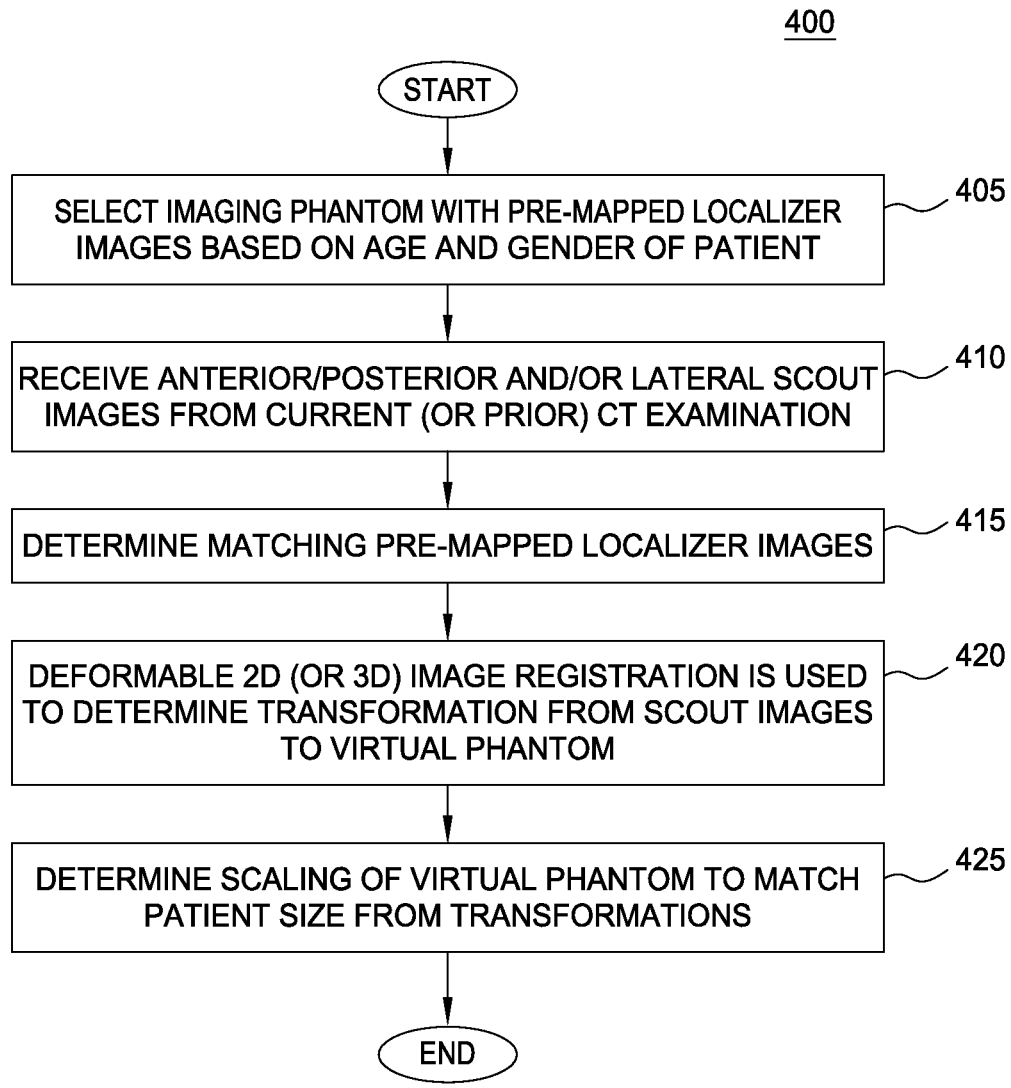
FIG. 4 illustrates a method for generating a suitable model for estimating patient radiation dose resulting from CT scans, according to one embodiment.

FIG. 4 illustrates a method 400 for generating a suitable model for estimating patient radiation dose resulting from CT scans, according to one embodiment. More specifically, method 400 illustrates an example embodiment where image registration techniques are used to deform a virtual phantom. As shown, the method 400 begins at step 405, where the dose estimation tool selects a virtual phantom with pre-mapped localizer images. As noted, the virtual phantom may be selected based on the age and gender of an individual receiving the CT scan procedure in question. At step 410, the dose estimation tool receives a scout image of the individual for whom the dose estimation is being performed. The scout image provides a 2D image projection of the individual, such as an anterior/posterior and/or lateral scout image taken by the CT scanning system prior to performing a full CT procedure. Alternatively, the scout image could be a 3D volume of the individual obtained as part of a prior CT scanning procedure. At step 415, the pre-mapped localizer images to use to deform the selected virtual phantom are obtained. The pre-mapped images may be selected based on the relevant regions of the patient to be scanned. For example, for a patient who will receive (or who received) a chest CT scan, the selected reference image may depict this region of an individual with a body geometry that closely matches the virtual phantom.

Figure 5:
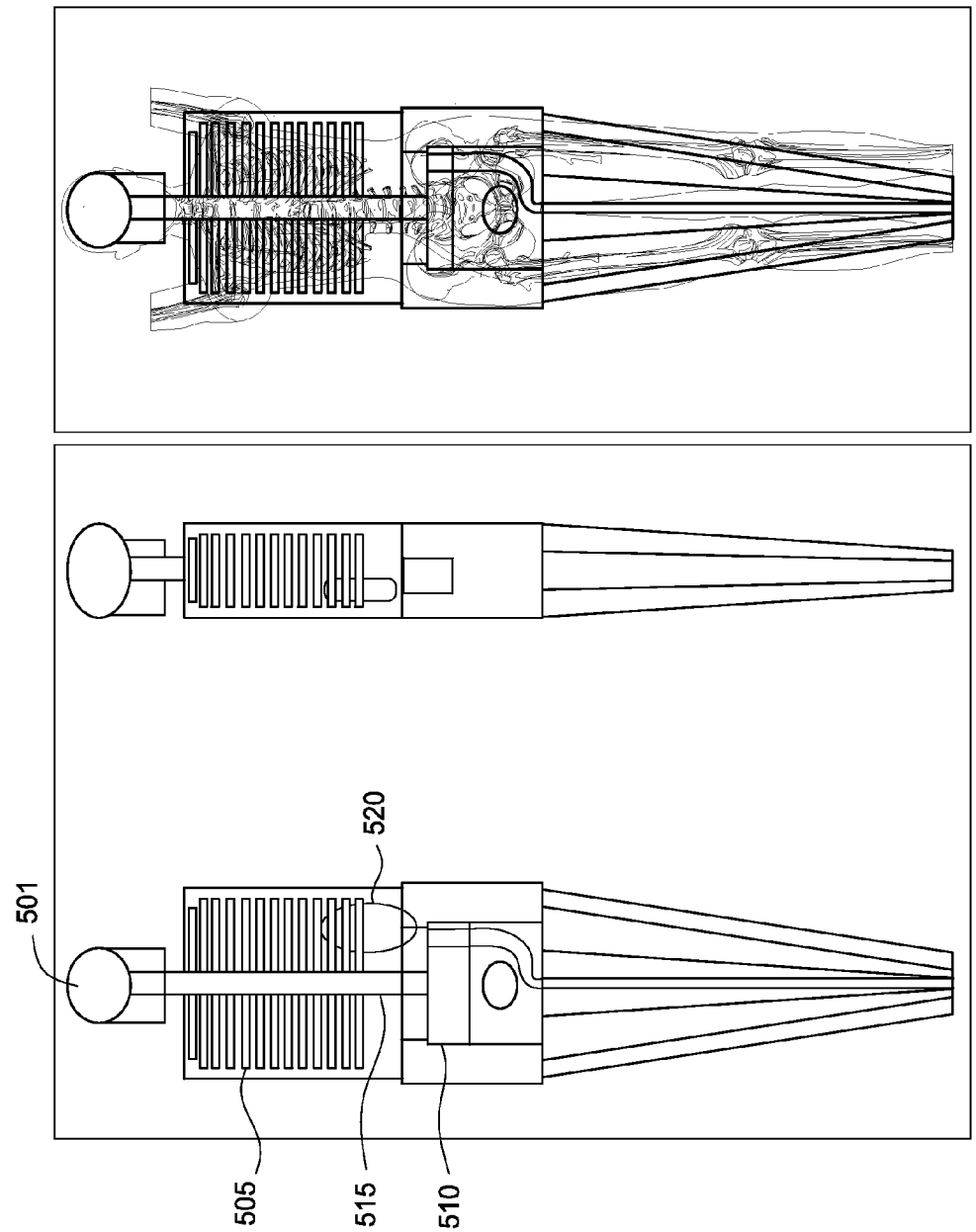
FIG. 5A illustrates an example image representing a deformable phantom, according to one embodiment.
FIG. 5B illustrates an example of a two-dimensional (2D) reference image of a portion of a human body corresponding to the phantom shown in FIG. 5A, according to one embodiment.

FIG. 5A illustrates an example image representing a deformable phantom, according to one embodiment. As shown, image 500 provides an anterior/posterior view 501 and a lateral view 502 of a virtual image phantom. As show in views 501 and 502, the geometry of this phantom includes a bone structure representing ribs 505, spine 515 and legs 522. Additionally, the views 501 and 502 include geometry representing organs, including a stomach 510 and a kidney 515. The virtual phantom (as depicted in views 501 and 502 provides a rough approximation of the size, shape, and positioning of human organs, tissues and structures.

While clearly a rough approximation of actual human anatomy, virtual phantoms are generally accepted as providing reasonably accurate estimates of dose absorption. FIG.

5B illustrates an example of a 2D reference image of a portion of a human body corresponding to the phantom shown in FIG. 5A, according to one embodiment. As shown, the relative positions, size, shape of the bones, tissues, organs, in the reference image match well to the corresponding positions in the virtual phantom.

Referring again to the method 400, at step 420, the dose estimation tool performs an image registration process to determine a transformation between the scout images of the patient and the reference images used to represent the virtual phantom. The result of the image registration is a mapping from points in the 2D scout localizer to points in the reference image (or vice-versa). Similarly, in cases of a 3D scout image of the patient (i.e., a current or prior CT scan), 3D image registration techniques may map points between the 3D scout image of the patient and points in a reference image corresponding to the phantom in a 3D coordinate space.

At step 425, this same transformation is used to deform the geometry representing the virtual phantom. By deforming the virtual phantom using transformations obtained from the image registration process, the size, shape, and organ positions represented by the geometry of the virtual phantom matches the geometry of the actual patient much more accurately. For example, performing an image registration process using the reference image shown in 5B and a scout localizer of a patient provides a transformation can be used to deform the virtual phantom shown in FIG. 5A. The deformed virtual phantom may be used to estimate organ absorbed dose resulting from a given CT procedure (either before or after such a procedure is performed). That is, the dose estimations obtained from a Monte Carlo simulation are tailored to the patient, as well as more accurate and more consistent when used to estimate patient dose over multiple scans.

Figure 6:
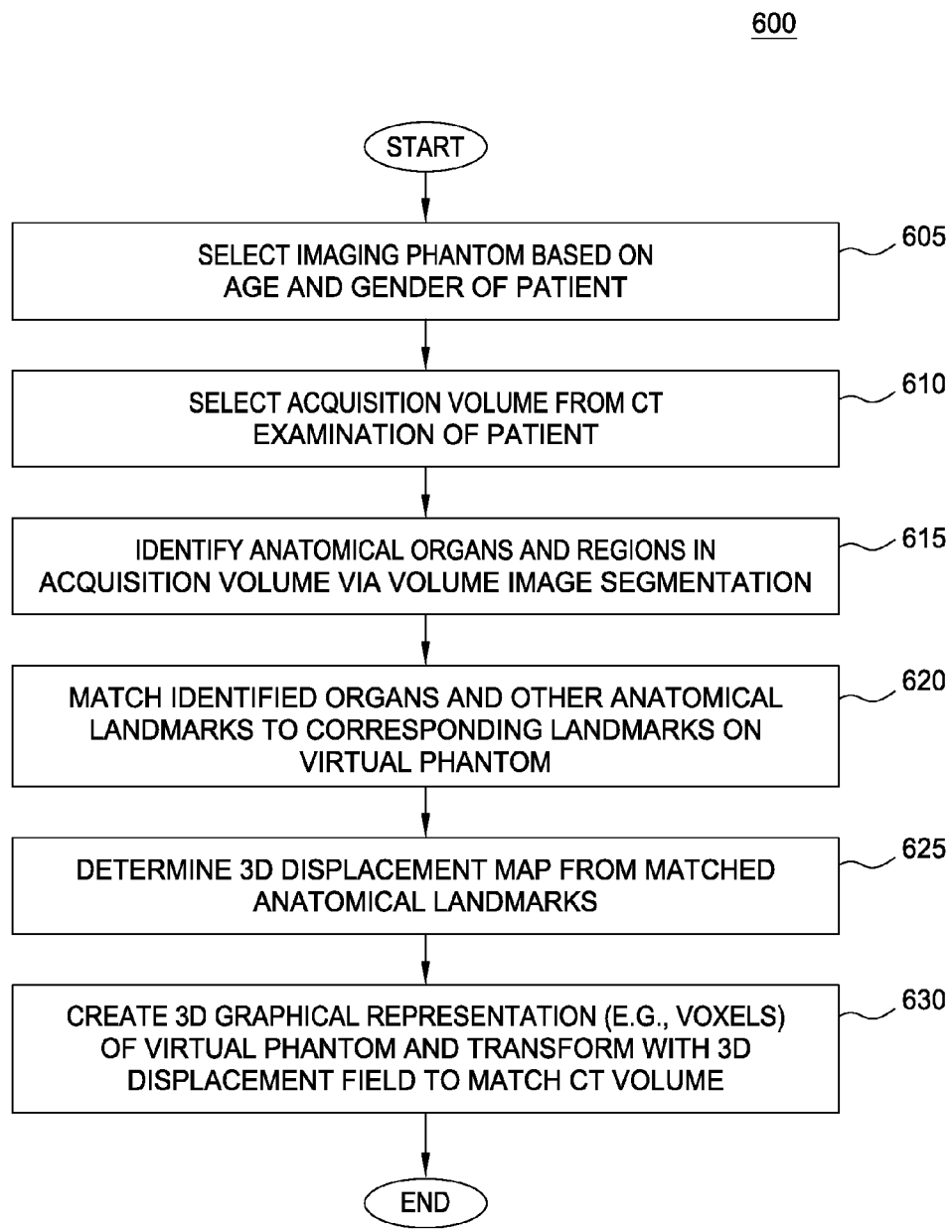
FIG. 6 illustrates another method for generating a suitable model for estimating radiation dose resulting from CT scans, according to one embodiment.

FIG. 6 illustrates another method for generating a suitable model for estimating radiation dose resulting from CT scans, according to one embodiment. More specifically, method 600 illustrates an example embodiment where image segmentation techniques are used to deform a virtual phantom. Like method 400, method 600 begins where the dose estimation tool selects an imaging phantom to deform, e.g., based on an age and gender of a patient (step 605). However, instead of retrieving 2D image localizers of the patient, the dose estimation tool receives a 3D scan volume of some portion of the patient (at step 610), e.g., a CT scan from a prior chest and abdomen CT. Once obtained, image segmentation is used to identify tissues, organs, structures, or other landmarks in the image volume (step 615). While a variety of available segmentation approaches can be used, in one embodiment, the image segmentation provides a minimal bounding box surrounding each identified organ or structure.

Figure 7:
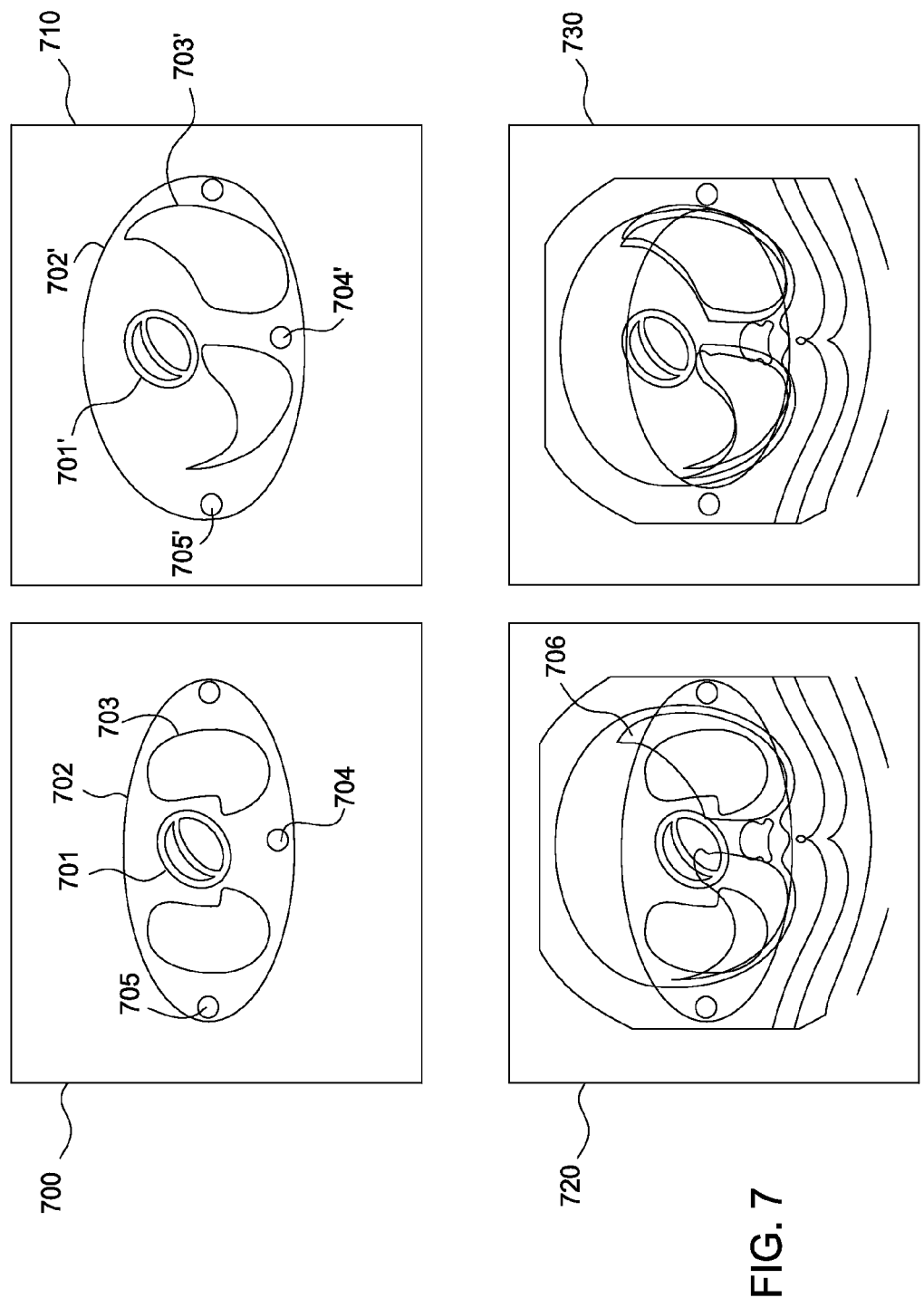
FIG. 7 illustrates an example slice of a phantom superimposed over a corresponding CT slice of a patient, according to one embodiment.

At step 620, the dose estimation tool matches the organs and other anatomical landmarks (e.g., bone position) identified in the CT scan segmentation with corresponding landmarks in the virtual phantom. For example, FIG. 7 illustrates an example slice of a CT scan superimposed over a corresponding slice of a virtual phantom, according to one embodiment. In this example, the virtual phantom slice 700 includes a line 702 representing the volume bounded by the phantom along with slice portions of a heart 701, lung 703, spine 704, and humerus bone 705. However, the location and position of the heart and lung organs in the virtual phantom do not correspond well with the position of these organs as depicted in the CT. For example, the open space region of the lungs (at 706) does not match the size or position of lungs 702 organs in the phantom. Similarly, the boundary line 702 of the phantom does not correspond well with the patient. Using this phantom to estimate dose, therefore, results in much greater dose absorption than would actually occur, because the phantom does not account for the large amounts of adipose tissues in this patient.

At the same time, other landmarks of the phantom line up well with the patient. For example, the spine and arms are generally collocated in both the phantom (spine 704 and humerus 705) and in the CT. Accordingly, at step 625, the dose estimation system, determines a 3D displacement map based on the matched anatomical or structural landmarks.

For example, in FIG. 7, phantom slice 700 shows an unmodified or un-deformed phantom and phantom slice 710 the same phantom slice after being displaced using the method of FIG. 6 (or after being deformed using an image registration technique according to the method of FIG. 4).

As shown in phantom slice 710, after being deformed using the identified organ volumes and displacement of a particular patient the boundary line 702' now more closely follows the contours of the patient CT scan, and the lungs 703' and heart 701' of the phantom have been displace to better reflect the position of these organs in the scan. At the same time, other anatomical landmarks such as the spine and humerus bone remain in the same general position. The imaging phantom shown in slice 700 is shown superimposed over the corresponding CT scan slice of a patient in slice 720. Similarly, the deformed phantom shown in slice 710 is shown superimposed over the corresponding CT scan slice of a patient in slice 730.

Referring again to FIG. 6, at step 630, the dose estimation tool generates a rasterized 3D representation of the displaced organs, tissues, and structures of the virtual phantom. As noted, above, the virtual phantom may be described as a series of non-uniform rational basis splines (NURBS), while the CT scan data is typically represented as a series of 3D coordinate single point values referred to as a "voxels"—short for "volume element," a voxel extends the concept of a pixel into a third dimension, and a variety of known approaches are available for "voxelizing" a collection of NURBs or CSG data. Doing so converts the geometric or mathematical representation of NURBs or CSG data into a 3D array of voxel values. In one embodiment, step 630 (the voxelization step) is performed in order to avoid discontinuities that often are a problem with Monte Carlo simulations in mathematical phantoms (whether NURB or CSG based). Further, voxel based models are well-suited to GPU-based computational methods to achieve improved speed.

Once the rasterized phantom is generated, it may be used to estimate organ absorbed dose resulting from a given CT procedure (either before or after such a procedure is performed). Like the image segmentation approaches, dose estimations performed using the phantom deformed using the segmentation approach are tailored to the patient, resulting in more accurate and more consistent dose estimates, both for individual and multiple scans.

Figure 8:
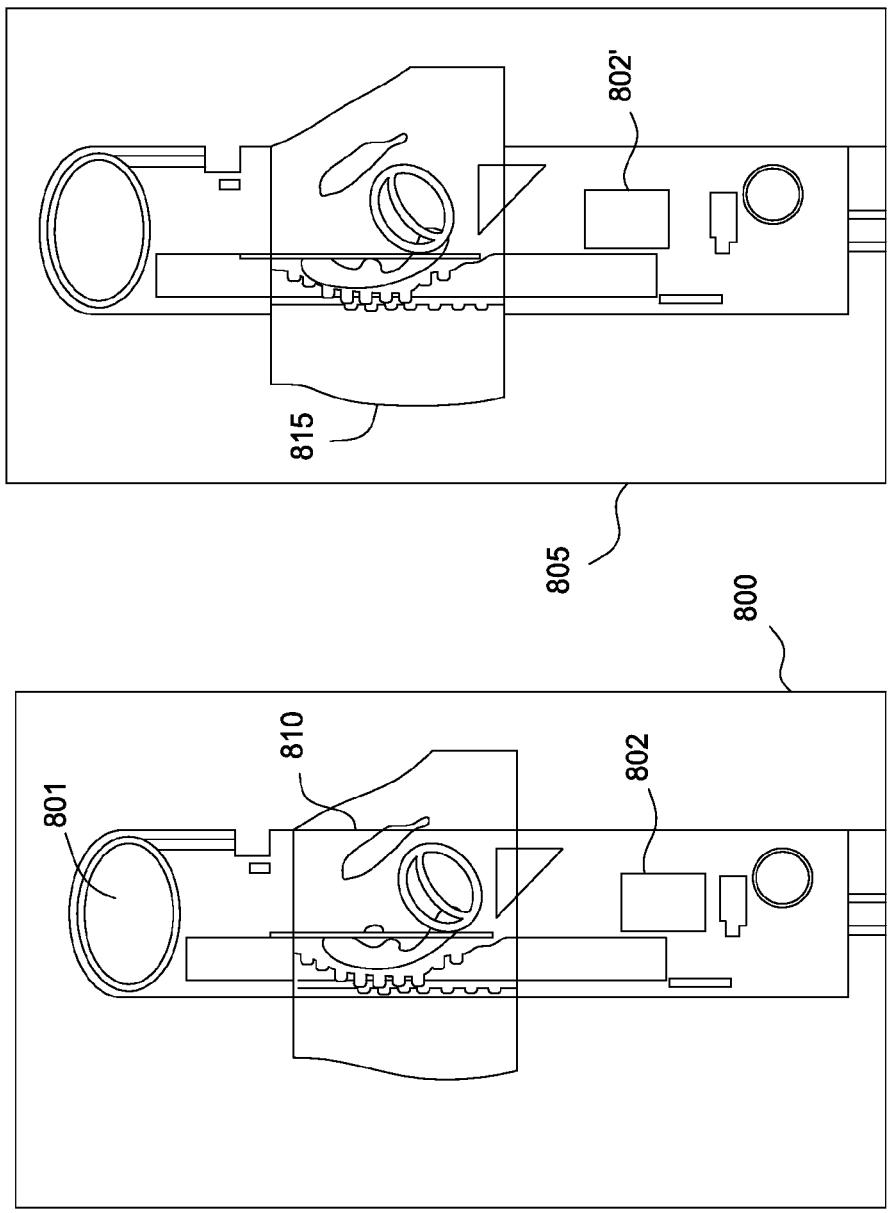
FIG. 8 illustrates an example of a transverse slice of an imaging phantom superimposed over a corresponding transverse CT slice of a patient, according to one embodiment.

FIG. 8 illustrates an example of a transverse slice of an imaging phantom superimposed over a corresponding transverse CT slice of a patient, according to one embodiment. In this example, a transverse view 800 corresponds to view 710 of FIG. 7 and a transverse view 805 corresponds to view 730 of FIG. 7. The transverse view is created by compositing a linear section of individual slices to create a longitudinal image. As shown, transverse views 800 and 805 provide a full length view including components not present in the superimposed CT image of the patient, e.g., brain 801 and kidney 802. As shown in view 800, a boundary 810 of the virtual phantom does not correspond well with the outline of the patient (i.e., with the body size bounded by the patient's skin). However, in view 805, a boundary 815 of the phantom has been displaced to better match the reference CT scan data of this patient. Similarly, internal organs, structures and other tissues may be displaced as well.

Importantly, this example illustrates that displacement may occur for elements of the virtual phantom that are not part of the CT scan data of the patient. For example, the kidney 802 could be displaced by the movement of other organs for which CT scan data is available, as shown by the displaced position of kidney 802' in view 805. Further, this example illustrates that a virtual phantom is required to estimate patient dose even where CT scan data is available. This occurs as although the CT scan in this example was limited to the chest and abdomen, X-ray scatter will result in some absorption by the brain, kidneys, and other organs and tissues of this patient. Stated differently, the virtual phantom is required to estimate organ dose absorption for organs not imaged as part of a given CT scan or procedure.

Figure 9:
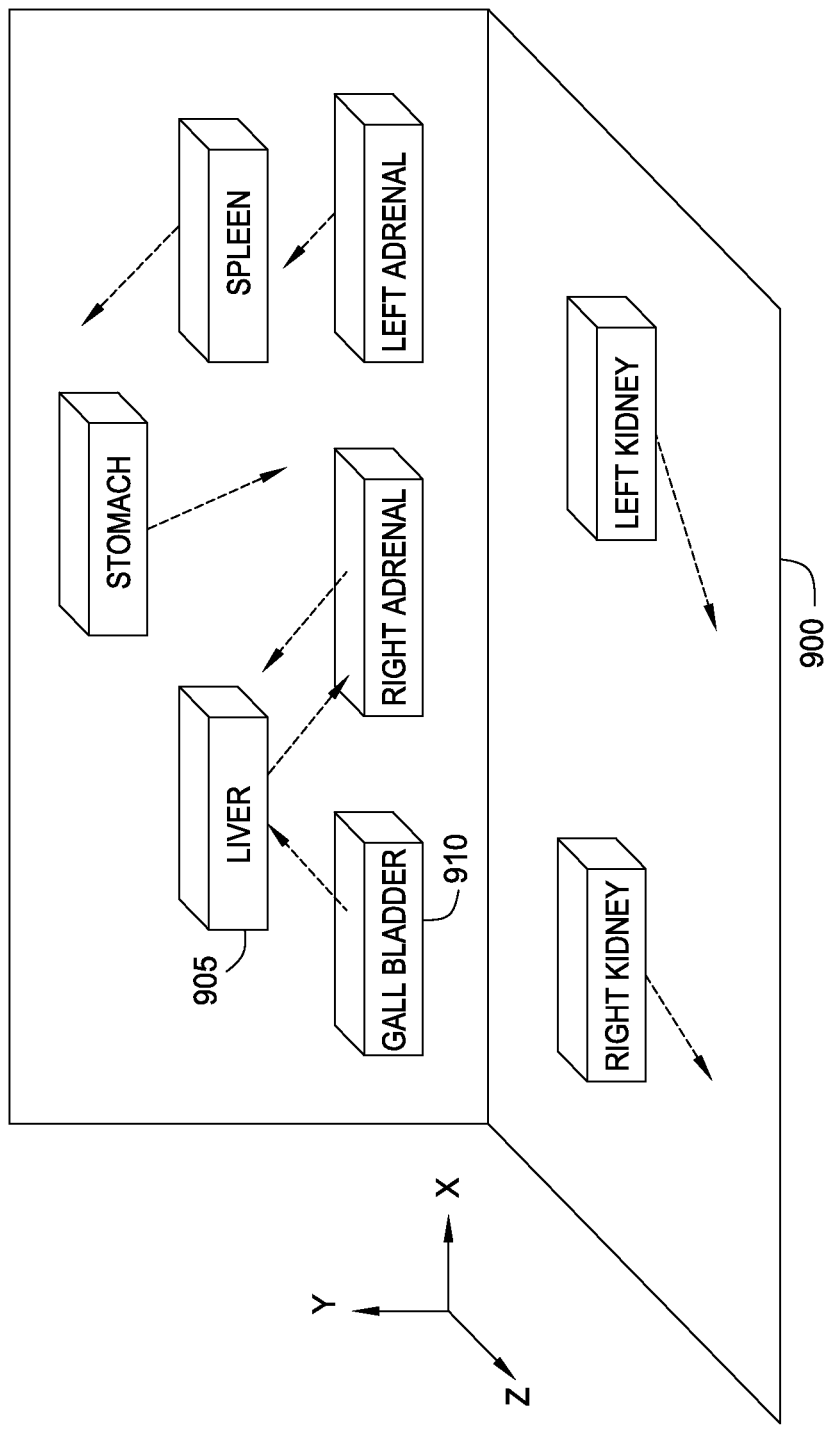
FIG. 9 illustrates an example of a CT image segmentation and organ volume displacement for an imaging phantom, according to one embodiment.

FIG. 9 illustrates another example of a CT image segmentation and organ volume displacement for an imaging phantom, according to one embodiment. In this example, a CT volume 900 corresponding to an imagining includes a set of bounding boxes representing a segmented image position for a variety of organs, e.g., liver 905, gall bladder 910, and right adrenal gland 915. Additionally, volume 900 shows arrows representing the displacement of these organs based on an image segmentation of CT scan data. In this particular example, the liver 905 has been displaced down and to the right, while gall bladder 910 has been displaced up and to the front of the liver 905 and right adrenal 915 has moved up and to the left into the space formerly occupied by the liver 905. Further, in this example, the organs are represented by bounding boxes, and are displaced based a geometric centroid. However, in an alternative embodiment image segmentation (for either the phantom or the CT image data of a patient) may provide a more accurate geometric volume representing an element of organ tissue or body structure. In such a case, the displacement could be based on a mass centroid of the organ, e.g., where the centroid of the liver is localized to one side based on mass or other approach that accounts for the topology of a given organ volume.

As illustrated in this example, displacing one organ (e.g., the liver 905) in a phantom based on its corresponding position in a CT reference scan, may require displacing other organs (e.g., the gall bladder 910 and right adrenal 915) as a result. This occurs as two organs plainly should not occupy the same physical volume when the phantom is used to perform a dose estimate analysis. Accordingly, in one embodiment, the dose estimation tool may displace organs, tissues or structures until reaching a "steady state."

Note, the example embodiments illustrated in FIGS. 4 and 6 may be used separately or in conjunction with one another to deform a virtual phantom. The particular approach or combination of approaches selected may be tailored to suit the needs in a particular case based on the available imaging phantoms, mapped 2D and/or 3D reference images, as well as on the availability and type of localizer scout images and/or prior CT scan data for a given patient.

Figure 10:
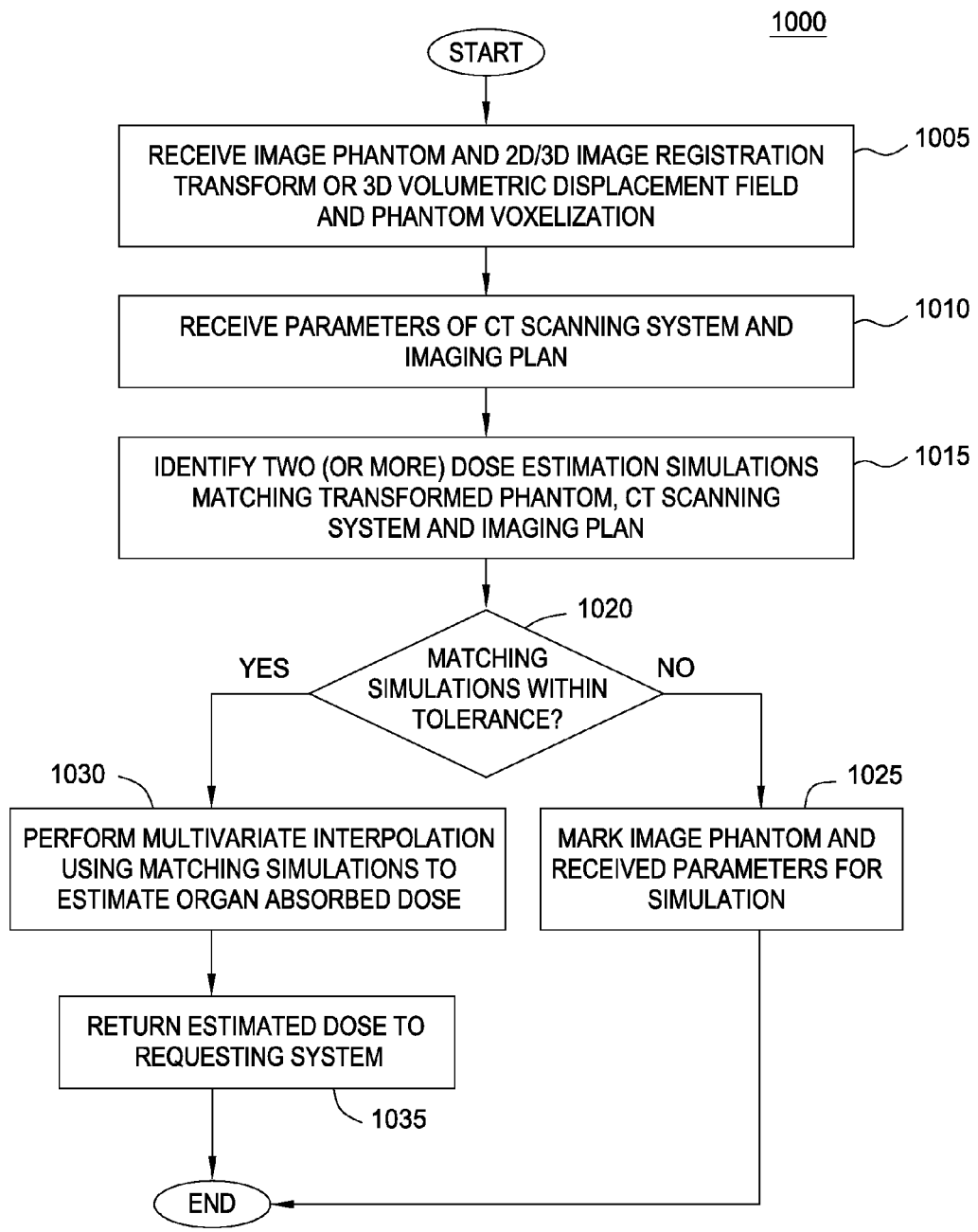
FIG. 10 illustrates a method for a dose estimation service to provide patient dose estimates to multiple CT scan providers, according to one embodiment.

In one embodiment, a cloud provider model host systems used to perform the dose estimates, maintain a library of computed simulations, as well as run the Monte Carlo simulations to augment the simulation library with new cases. For example, FIG. 10 illustrates a method 1000 for a dose estimation service to provide patient dose estimates to multiple CT scan providers.

As shown, the method 1000 begins at step 1005 where the dose estimation service receives an image phantom (or a reference to an image phantom) along with 2D or 3D image registration transforms or 3D volumetric displacement field and phantom voxelization. In an alternative embodiment, the dose estimation service may receive data describing the deformed phantom such as the transformed NURBS resulting from the 2D or 3D image registration process or CT field displacement techniques described above.

At step 1010, the dose estimation services receives parameters of a CT scanning system and an imaging plan for a CT scan performed (or to be performed) on a patient. Once the parameters of the patient, scanning equipment, and CT scan provider are received, the dose estimation service may identify two (or more) simulations in the library matching the transformed phantom, CT scanning system parameters and imaging plan (step 1015). The provider can set customizable tolerances to be set for each variable (e.g., actual kVp is within 10 kV of simulation). Further evaluating simulations, only simulations within tolerance for all (or specified set) of the given parameters are factored into the calculation. In one embodiment, the simulation results may be interpolated using the known Shepard's method. The standard deviation across the set of simulation results is used as a measure of uncertainty (e.g. for the set of 5 simulations used, absorbed dose to the breasts has a SD of 0.2 mSv and absorbed dose to the liver has a SD of 0.15 mSv).

At step 1020, the dose estimation service determines whether the matching simulations identified at step 1015 are within a tolerance parameter (or meets other thresholds or criteria). If not, then the image phantom (and deformations/transformations) and received parameters are added to a queue of patient/scanner/image plan scenarios to simulate (step 1025). As noted, the simulation may use Monte Carlo simulation techniques to determine estimates of organ absorbed dose tailored to both the individual patient (based on the deformed phantom and the particular imaging facility based on the CT scanner and calibration/setting data.

However, as the simulation library of a SaaS provider grows, most requests should identify a set of simulations to interpolate. At step 1030, the dose estimation service performs a multivariate scatter interpolation using the matching simulations identified at step 1015 to estimate organ absorbed dose for a particular patient and associated CT scanning procedure. Note, such an analysis may be performed much more quickly than a full Monte Carlo simulation, allowing dose estimates to keep pace with a sequence of procedures performed at a given imaging facility (or facilities) as well as being provided concurrent with a given procedure (e.g., to ensure cumulative dose limits are not exceeded). In one embodiment, the multivariate scatter interpolation method currently used is referred to as 'Shepard's method'. Examples of this method are described in Shepard, Donald (1968). "A two-dimensional interpolation function for irregularly-spaced data". *Proceedings of the* 1968 *ACM National Conference*. pp. 517-524.

At step 1035, once the interpolation process is complete, dose estimates are returned to a requesting system (e.g., a dose estimate client program running on a computing system at an imaging facility). At the client a dose management system tracks patient organ equivalent dose, effective dose, CTDI, DLP, DAP down to the examination level. This information is also summed up to provide cumulative tracking of organ equivalent dose, effective dose, CTDI, DLP, DAP for a given patient's history. Further aggregation of this information is used to provide institution-wide presentation of per capita organ equivalent dose, patient effective dose, CTDI, DLP, DAP. Thus, the dose estimation service may provide an imaging facility with a broad variety of. This same information is available to an imaging facility that runs a local instance of the dose estimation system.

Figure 11:
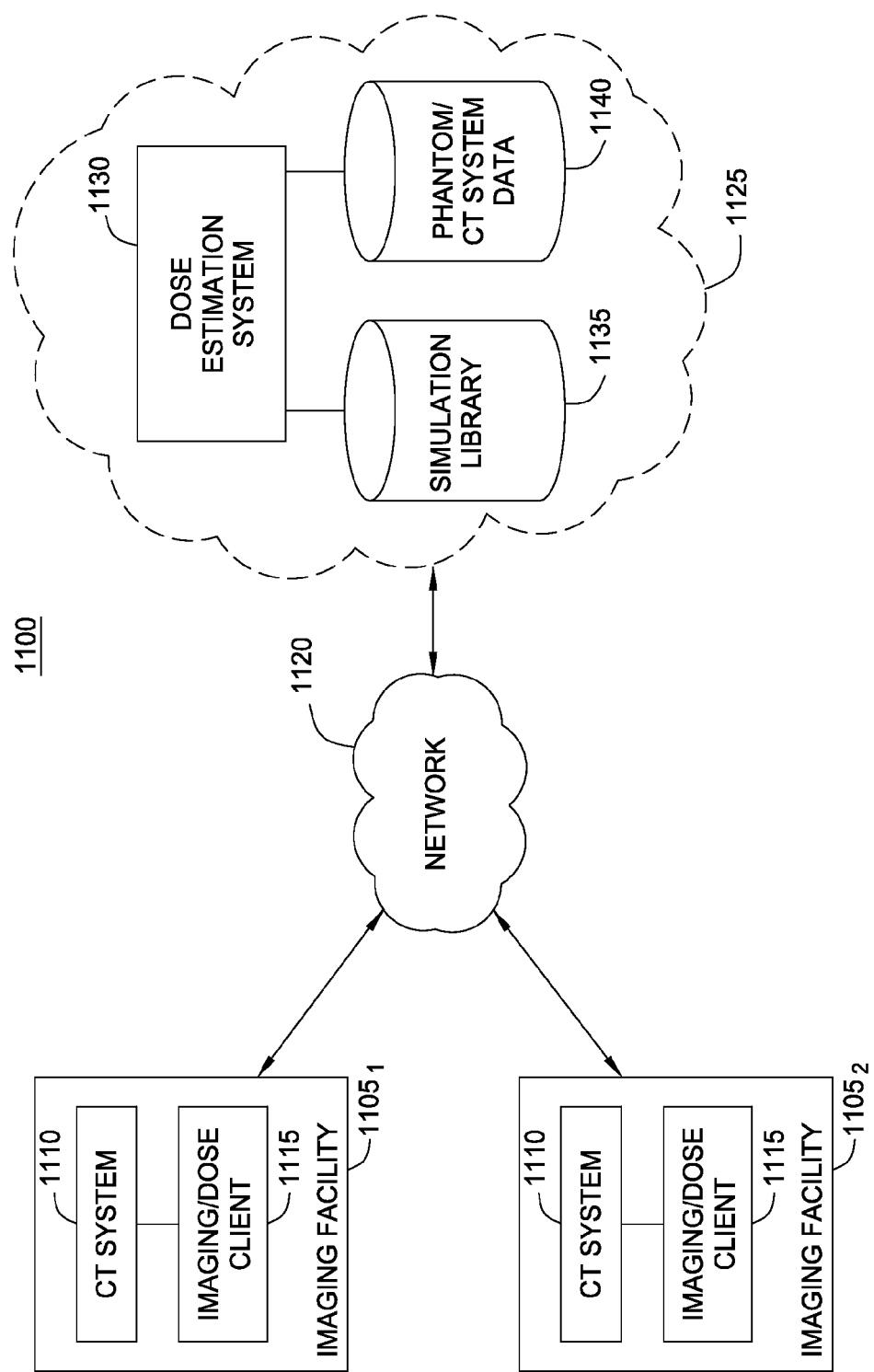
FIG. 11 illustrates an example computing infrastructure for a patient dose estimation service system configured to support multiple CT scan providers, according to one embodiment.
Figure 9:
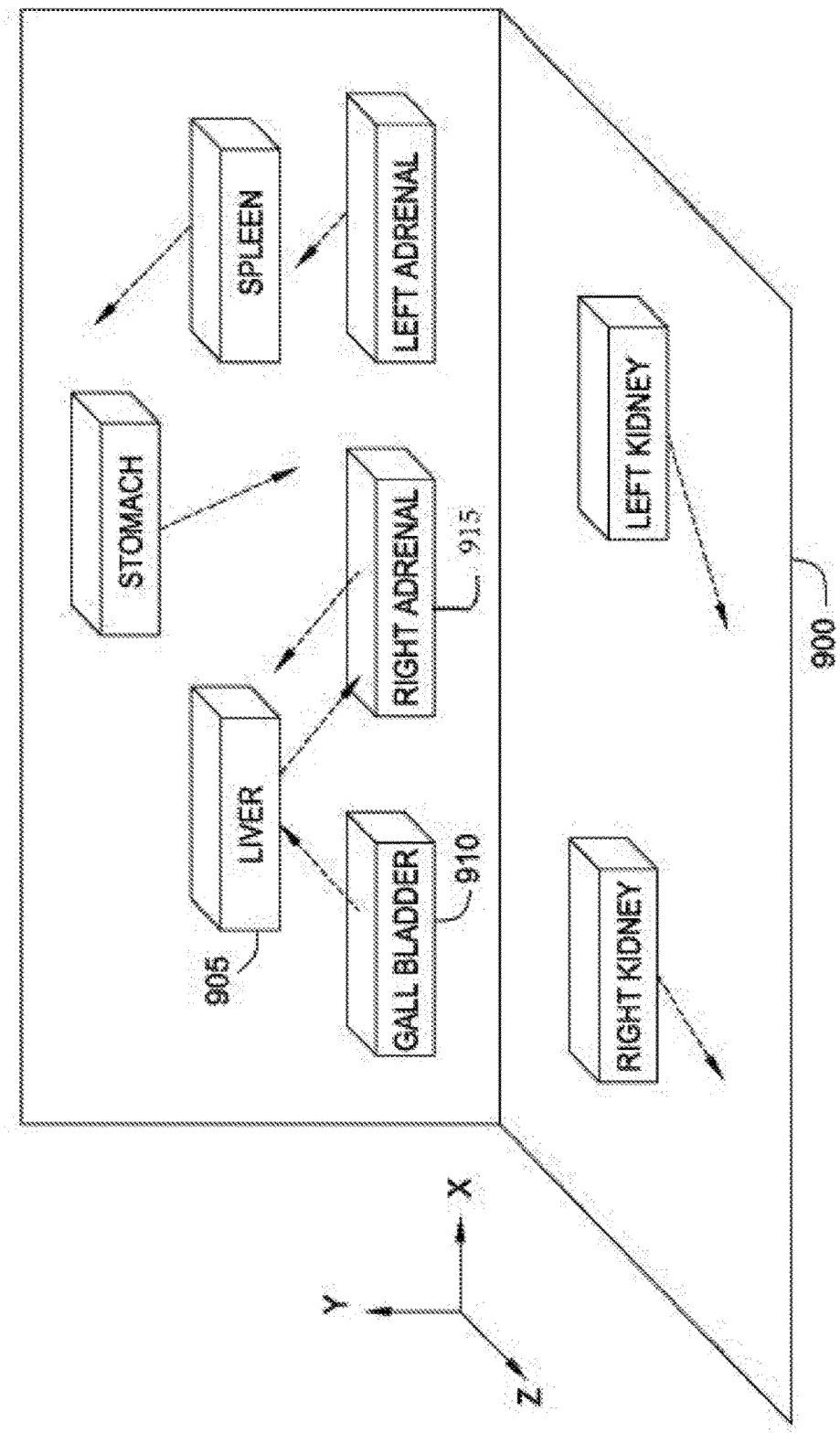
Figure 11:
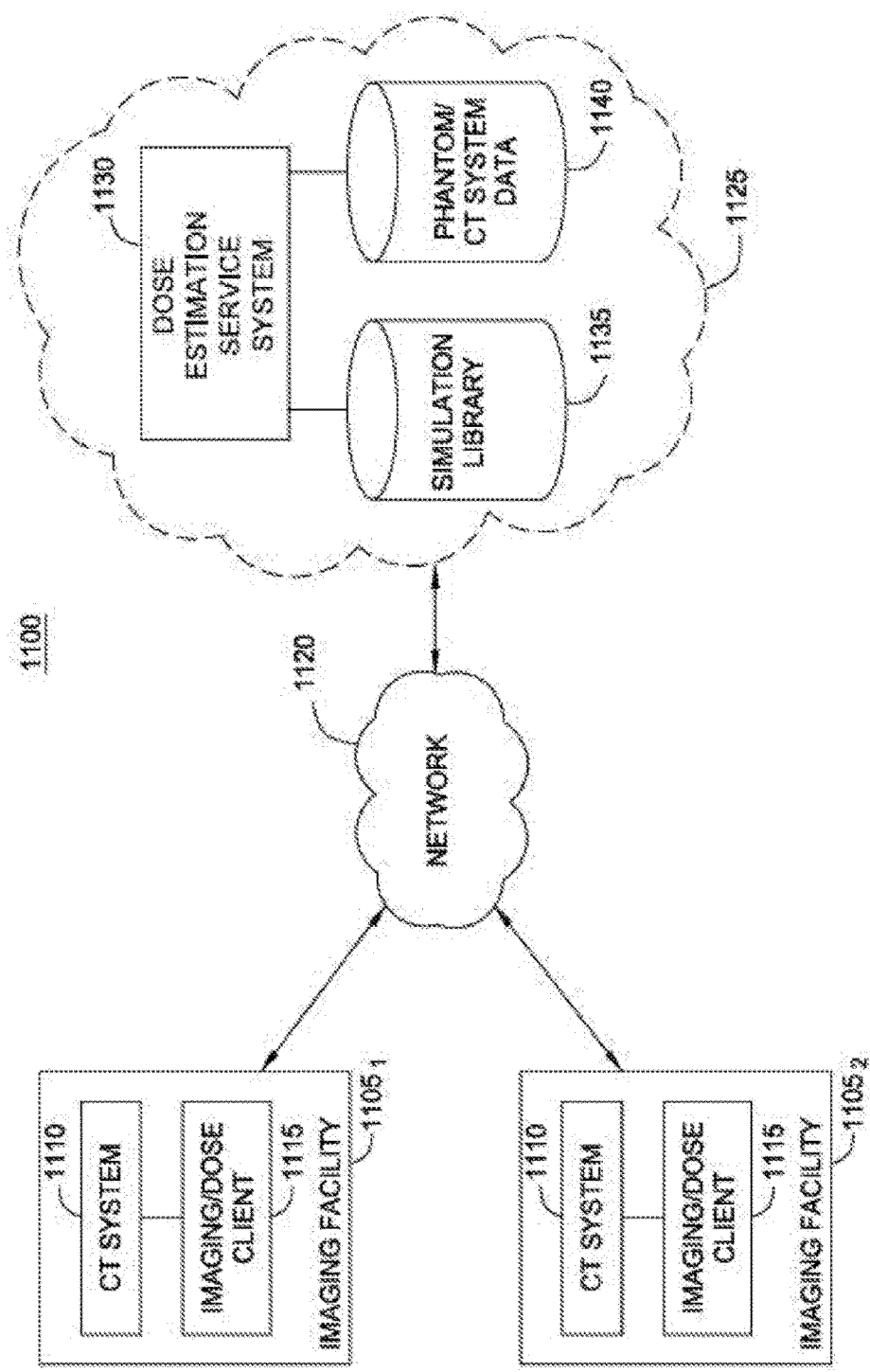

FIG. 11 illustrates an example computing infrastructure 1100 for a patient dose estimation service system configured to support multiple CT scan providers, according to one embodiment. As shown, a cloud based provider 1125 hosting a dose estimation service 1130 receives requests for dose estimates over network 1120 from imaging facilities 1105$_{1\text{-}2}$. At each imaging facility 1105, a CT system 1110 is used to provide imaging services for patients. An imaging/dose client 1115 communicates with the dose estimation service 1130 to request and receive estimates of patient dose, where the dose estimates are tailored based on the procedure and patient. As noted, the request may include parameters for a CT procedure, scanning equipment and modality, and a deformed phantom (or transformations used to deform a phantom) based on the body morphology of the particular patient.

At the dose estimation service 1130, a simulation library 1135 is used to select simulations for interpolating an amount of patient dose using data in the request and modules of a CT scanner and procedures (shown in FIG. 11 a phantom/CT system data 1140). If no good candidate simulations are available for interpolation, then the service 1130 may add the request to a queue of simulations to perform. Monte Carlo simulations are then performed in response to the request, providing both an estimate of patient dose for a given patient and imaging procedure as well as a new simulation data point to add to the library 1125.

Advantageously, embodiments of the invention provide a variety of techniques for estimating radiation doses that result from CT (and other) X-ray imaging techniques. As described, image registration techniques and/or image segmentation techniques may be used to create a hybrid imaging phantom that more accurately matches an individual's body size shape. Doing so improves the accuracy of dose estimates determined from a simulation. That is, the resulting hybrid phantom provides a much more accurate mathematical representation of a particular patient to use in a dose simulation than the unmodified phantoms alone.

Once the transformations are determined, the hybrid virtual phantom may be used to simulate a given CT procedure for the patient. For example, Monte Carlo simulation techniques may be used to estimate organ absorbed dose for a virtual phantom. Such simulation techniques use the virtual phantom (as transformed relative to a given patient), along with a number of parameters related to the CT scanner model and procedure to be performed in order to compute accurate estimates of organ absorbed dose. However, estimating organ absorbed organ dose using a Monte Caro simulation can require significant amounts of computing time, much longer than required to perform an actual CT scan. Accordingly, in one embodiment, estimates of patient dose determined for a given procedure may be generated by interpolating between two (or more) previously completed simulations. If no "close" simulations are available, then the hybrid virtual phantom, CT scanner and procedure data may be added to a queue of full Monte Carlo simulations to be performed. Over time, a large library of simulations allows for dose estimates to be provided in real time as procedures are scheduled and performed. Doing so allows cumulative dose amounts for a given patient to be captured, as well as cumulative dose limits to be observed. Further, in one embodiment, a SaaS provider is a hosted dose estimation service provided to multiple imaging facilities. In such a case, the service provider may have a robust library of simulations to use in interpreting dose estimates for the imaging providers.

While the foregoing is directed to embodiments of the present invention, other and further embodiments of the invention may be devised without departing from the basic scope thereof, and the scope thereof is determined by the claims that follow.

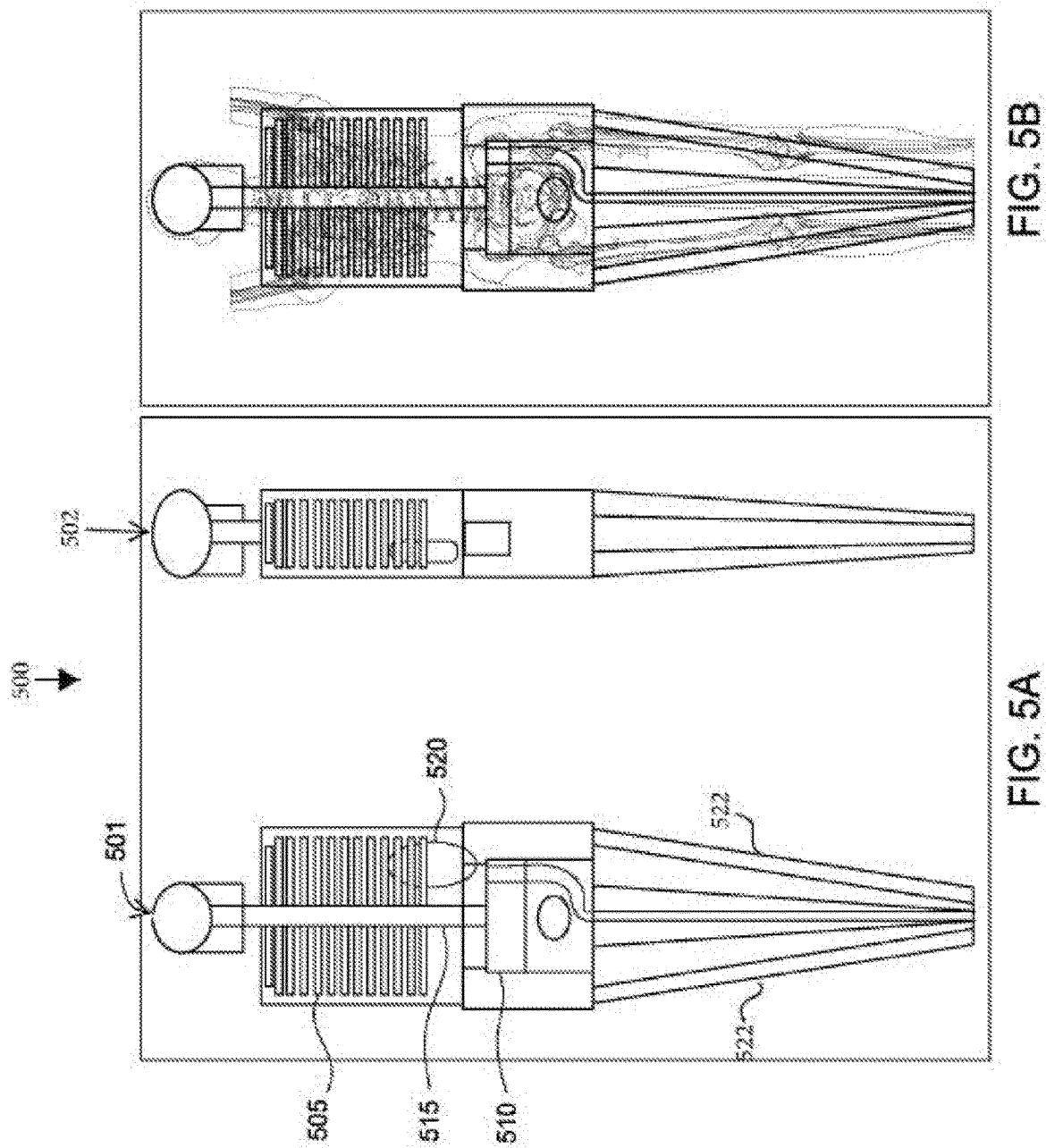

What is claimed is:

1. A computer-implemented method for providing a plurality of medical imaging providers with estimates of radiation dose absorbed by individuals receiving imaging scans, the method comprising:
   receiving, from one of the medical imaging providers, a request for an estimate of radiation dose absorbed by an individual in receiving an imaging scan, wherein the request identifies an imaging phantom, a transformation for deforming the imaging phantom, and a set of parameters describing the imaging scan and an image scanning apparatus being used to perform the imaging scan;
   deforming the imaging phantom based on the transformation;
   evaluating a plurality of dose estimation simulations estimating radiation dose absorption;
   upon determining, based on the evaluation, that two or more of the plurality of simulations match the received set of parameters and the deformed imaging phantom within a specified tolerance measure, interpolating the estimates of radiation dose in the two or more simulations to determine the estimate of radiation dose absorbed by the individual in receiving the imaging scan;
   upon determining, based on the evaluation, that the plurality of simulations do not include at least two simulations matching the received set of parameters and the deformed imaging phantom within the specified tolerance measure:
      performing a simulation of the imaging scan using the deformed imaging phantom and the received set of parameters;
      estimating, based on the simulation, amounts of radiation absorbed by the individual as a result of performing the imaging scan; and
      adding the performed simulation to the plurality of dose estimation simulations; and
   returning, to the medical imaging provider, one of the interpolated estimate of patient dose or the estimated amounts of absorbed radiation from performing the simulation of the imaging scan.

2. The method of claim 1, wherein the imaging scan is a computerized tomography (CT) scan.

3. The method of claim 1, wherein the interpolation is a multivariate scatter interpolation.

4. The method of claim 1, wherein the simulation is a Monte Carlo simulation.

5. The method of claim 1, wherein the transformation for deforming the imaging phantom is determined by performing an image registration process mapping a set of points in at least one localizer image associated with the imaging phantom to a corresponding set of points in a scout image of the individual.

6. The method of claim, 1 wherein the transformation for deforming the imaging phantom is determined by:
   segmenting a reference CT scan associated with the individual to identify a three-dimensional (3D) position of a plurality of anatomical landmarks of the individual present in the reference CT scan;

matching one or more of the identified anatomical landmarks in the segmented reference CT scan to corresponding anatomical landmarks in the imaging phantom;

determining a three dimensional (3D) displacement map from the matched anatomical landmarks;

voxelizing the imaging phantom; and determining an image transformation for transforming the voxelized imaging phantom to match the displacement map.

7. A non-transitory computer-readable storage medium storing one or more application programs, which, when executed by a processor performs an operation for providing a plurality of medical imaging providers with estimates of radiation dose absorbed by individuals receiving imaging scans, the operation comprising:

receiving, from one of the medical imaging providers, a request for an estimate of radiation dose absorbed by an individual in receiving an imaging scan, wherein the request identifies an imaging phantom, a transformation for deforming the imaging phantom, and a set of parameters describing the imaging scan and an image scanning apparatus being used to perform the imaging scan;

deforming the imaging phantom based on the transformation;

evaluating a plurality of dose estimation simulations estimating radiation dose absorption;

upon determining, based on the evaluation, that two or more of the plurality of simulations match the received set of parameters and the deformed imaging phantom within a specified tolerance measure, interpolating the estimates of radiation dose in the two or more simulations to determine the estimate of radiation dose absorbed by the individual in receiving the imaging scan;

upon determining, based on the evualuation, that the plurality of simulations do not include at least two simulations matching the received set of parameters and the deformed imaging phantom within the specified tolerance measure:

performing a simulation of the imaging scan using the deformed imaging phantom and the received set of parameters;

estimating, based on the simulation, amounts of radiation absorbed by the individual as a result of performing the imaging scan; and adding the performed simulation to the plurality of dose estimation simulations; and returning, to the medical imaging provider, one of the interpolated estimate of patient dose or the estimated amounts of absorbed radiation from performing the simulation of the imaging scan.

8. The computer-readable storage medium of claim 7, wherein the imaging scan is a computerized tomography (CT) scan.

9. The computer-readable storage medium of claim 7, wherein the interpolation is a multivariate scatter interpolation.

10. The computer-readable storage medium of claim 7, wherein the simulation is a Monte Carlo simulation.

11. The computer-readable storage medium of claim 7, wherein the transformation for deforming the imaging phantom is determined by performing an image registration process mapping a set of points in at least one localizer image associated with the imaging phantom to a corresponding set of points in a scout image of the individual.

12. The computer-readable storage medium of claim 7, wherein the transformation for deforming the imaging phantom is determined by:

segmenting a reference CT scan associated with the individual to identify a three-dimensional (3D) position of a plurality of anatomical landmarks of the individual present in the reference CT scan;

matching one or more of the identified anatomical landmarks in the segmented reference CT scan to corresponding anatomical landmarks in the imaging phantom;

determining a three dimensional (3D) displacement map from the matched anatomical landmarks;

voxelizing the imaging phantom; and determining an image transformation for transforming the voxelized imaging phantom to match the displacement map.

13. A system, comprising:

a processor; and a memory storing an application program configured to perform an operation for providing a plurality of medical imaging providers with estimates of radiation dose absorbed by individuals receiving imaging scans, the operation comprising:

receiving, from one of the medical imaging providers, a request for an estimate of radiation dose absorbed by an individual in receiving an imaging scan, wherein the request identifies an imaging phantom, a transformation for deforming the imaging phantom, and a set of parameters describing the imaging scan and an image scanning apparatus being used to perform the imaging scan, deforming the imaging phantom based on the transformation, evaluating a plurality of dose estimation simulations estimating radiation dose absorption, and upon determining, based on the evaluation, that two or more of the plurality of simulations match the received set of parameters and the deformed imaging phantom within a specified tolerance measure, interpolating the estimates of radiation dose in the two or more simulations to determine the estimate of radiation dose absorbed by the individual in receiving the imaging scan;

upon determining, based on the evaluation, that the plurality of simulations do not include at least two simulations matching the received set of parameters and the deformed imaging phantom within the specified tolerance measure:

performing a simulation of the imaging scan using the deformed imaging phantom and the received set of parameters;

estimating, based on the simulation, amounts of radiation absorbed by the individual as a result of performing the imaging scan; and adding the performed simulation to the plurality of dose estimation simulations; and returning, to the medical imaging provider, one of the interpolated estimate of patient dose or the estimated amounts of absorbed radiation from performing the simulation of the imaging scan.

14. The system of claim 13, wherein the imaging scan is a computerized tomography (CT) scan.

15. The system of claim 13, wherein the interpolation is a multivariate scatter interpolation.

16. The system of claim 13, wherein the simulation is a Monte Carlo simulation.

17. The system of claim 13, wherein the transformation for deforming the imaging phantom is determined, by the medical imaging provider submitting the request, by performing an image registration process mapping a set of points in at least one localizer image associated with the imaging phantom to a corresponding set of points in a scout image of the individual.

18. The system of claim 13, wherein the transformation for deforming the imaging phantom is determined, by the medical imaging provider submitting the request, by:
- segmenting a reference CT scan associated with the individual to identify a three-dimensional (3D) position of a plurality of anatomical landmarks of the individual present in the reference CT scan;
- matching one or more of the identified anatomical landmarks in the segmented reference CT scan to corresponding anatomical landmarks in the imaging phantom;
- determining a three dimensional (3D) displacement map from the matched anatomical landmarks;
- voxelizing the imaging phantom; and
- determining an image transformation for transforming the voxelized imaging phantom to match the displacement map.

* * * * *

UNITED STATES PATENT AND TRADEMARK OFFICE
CERTIFICATE OF CORRECTION

PATENT NO.         : 8,958,617 B2                                Page 1 of 5
APPLICATION NO.    : 13/315208
DATED              : February 17, 2015
INVENTOR(S)        : Couch et al.

It is certified that error appears in the above-identified patent and that said Letters Patent is hereby corrected as shown below:

In the Drawings
Replace FIG. 5A with FIG. 5A as shown on the attached page.
Replace FIG. 9 with FIG. 9 as shown on the attached page.
Replace FIG. 11 with FIG. 11 as shown on the attached page.

In the Specification
In Column 3, Line 26, delete "an example" and insert -- an example of --, therefor.
In Column 4, Line 67, delete "preformed" and insert -- performed --, therefor.
In Column 8, Line 47, delete "virtual imaging phantom 122" and insert -- virtual imaging phantom 132 --, therefor.
In Column 9, Line 53, delete "the a" and insert -- the --, therefor.
In Column 9, Line 59, delete "example an" and insert -- example of an --, therefor.
In Column 9, Line 60, delete "mange" and insert -- manage --, therefor.
In Column 9, Line 63, delete "CT system interface 214 network interface 215" and insert -- network interface 215 --, therefor.
In Column 9, Line 64, delete "memory 225" and insert -- memory 220 --, therefor.
In Column 10, Line 2, delete "memory 225" and insert -- memory 220 --, therefor.
In Column 10, Line 3, delete "memory 225" and insert -- memory 220 --, therefor.
In Column 10, Line 7, delete "memory 225" and insert -- memory 220 --, therefor.
In Column 10, Line 9, delete "memory 225" and insert -- memory 220 --, therefor.
In Column 10, Lines 14-15, delete "network attached (NAS)," and insert -- network attached storage (NAS), --, therefor.
In Column 10, Lines 20-21, delete "dose estimation interface 226. And the storage 235" and insert -- dose estimation interface 226, and the storage 230 --, therefor.
In Column 10, Line 58, delete "interconnect 320" and insert -- interconnect 317 --, therefor.
In Column 10, Line 59, delete "memory 325" and insert -- memory 320 --, therefor.
In Column 10, Line 65, delete "memory 325" and insert -- memory 320 --, therefor.
In Column 11, Line 3, delete "memory 325" and insert -- memory 320 --, therefor.
In Column 11, Lines 6-7, delete "solid state (SSD) storage drive," and insert -- solid state storage drive (SSD), --, therefor.

Signed and Sealed this
Eighteenth Day of August, 2020

Andrei Iancu
*Director of the United States Patent and Trademark Office*

CERTIFICATE OF CORRECTION (continued)
U.S. Pat. No. 8,958,617 B2

In Column 11, Line 15, delete "simulation library 336" and insert -- simulation library 335 --, therefor.
In Column 11, Line 18, delete "imaging phantom data 322" and insert -- imaging phantom data 332 --, therefor.
In Column 11, Lines 52-53, delete "dose estimation server 130," and insert -- dose estimation system 130, --, therefor.
In Column 12, Line 61, delete "kidney 515." and insert -- kidney 520. --, therefor.
In Column 13, Line 64, delete "lungs 702" and insert -- lungs 703 --, therefor.
In Column 16, Line 34, delete "(based" and insert -- based --, therefor.
In Column 17, Line 7, delete "dose estimation service 1130" and insert -- dose estimation service system 1130 --, therefor.
In Column 17, Line 11, delete "dose estimation service 1130" and insert -- dose estimation service system 1130 --, therefor.
In Column 17, Line 19, delete "dose estimation service 1130" and insert -- dose estimation service system 1130 --, therefor.
In Column 17, Line 24, delete "service 1130" and insert -- service system 1130 --, therefor.
In Column 17, Line 29, delete "library 1125" and insert -- library 1135 --, therefor.

In the Claims
In Column 18, Line 62, Claim 6, delete "claim, 1" and insert -- claim 1, --, therefor.
In Column 19, Line 37, Claim 7, delete "evualuation" and insert -- evaluation --, therefor.